(12) United States Patent
Kuroda et al.

(10) Patent No.: US 10,934,542 B2
(45) Date of Patent: Mar. 2, 2021

(54) ARTIFICIAL MATCH-TYPE MIRNA FOR CONTROLLING GENE EXPRESSION AND USE THEREFOR

(71) Applicants: BONAC CORPORATION, Kurume (JP); TOKYO MEDICAL UNIVERSITY, Tokyo (JP)

(72) Inventors: Masahiko Kuroda, Tokyo (JP); Shinichiro Ohno, Tokyo (JP); Eriko Aoki, Kurume (JP); Yasuhiko Yoshida, Kurume (JP); Shiori Kato, Kurume (JP); Tadaaki Ohgi, Kurume (JP)

(73) Assignees: BONAC CORPORATION, Kurume (JP); TOKYO MEDICAL UNIVERSITY, Tokyo (JP)

( * ) Notice: Subject to any disclaimer, the term of this patent is extended or adjusted under 35 U.S.C. 154(b) by 0 days.

(21) Appl. No.: 15/108,453

(22) PCT Filed: Dec. 27, 2014

(86) PCT No.: PCT/JP2014/084724
§ 371 (c)(1),
(2) Date: Jun. 27, 2016

(87) PCT Pub. No.: WO2015/099187
PCT Pub. Date: Jul. 2, 2015

(65) Prior Publication Data
US 2016/0319282 A1    Nov. 3, 2016

(30) Foreign Application Priority Data

Dec. 27, 2013   (JP) .............................. JP2013-273033

(51) Int. Cl.
*C12N 15/11*      (2006.01)
*C12N 15/113*     (2010.01)
*A61K 31/713*     (2006.01)

(52) U.S. Cl.
CPC .......... *C12N 15/113* (2013.01); *A61K 31/713* (2013.01); *C12N 2310/141* (2013.01); *C12N 2310/318* (2013.01); *C12N 2310/531* (2013.01)

(58) Field of Classification Search
CPC ............ C12N 15/113; C12N 2310/141; C12N 2310/531
See application file for complete search history.

(56) References Cited

U.S. PATENT DOCUMENTS

| | | | |
|---|---|---|---|
| 3,687,808 A | 8/1972 | Merigan, Jr. et al. |
| 4,550,163 A | 10/1985 | Voss et al. |
| 6,905,827 B2 | 6/2005 | Wohlgemuth et al. |
| 7,579,148 B2 | 8/2009 | Wohlgemuth et al. |
| 7,595,301 B2 | 9/2009 | Kunugiza et al. |
| 7,604,936 B2 | 10/2009 | Wohlgemuth et al. |
| 7,655,768 B2 | 2/2010 | Ohgi et al. |
| 7,771,950 B2 | 8/2010 | Wohlgemuth et al. |
| 8,110,364 B2 | 2/2012 | Wohlgemuth et al. |
| 8,691,782 B2 | 4/2014 | Ohgi et al. |
| 8,785,121 B2 | 7/2014 | Ohgi et al. |
| 8,933,046 B2 | 1/2015 | Machuy et al. |
| 9,206,422 B2 | 12/2015 | Ohgi et al. |
| 9,528,111 B2 | 12/2016 | Ohgi et al. |
| 9,663,784 B2 | 5/2017 | Ohgi et al. |
| 10,238,752 B2 | 3/2019 | Ohgi et al. |
| 2002/0042059 A1 | 4/2002 | Makarov et al. |
| 2002/0156261 A1 | 10/2002 | Malvy et al. |
| 2003/0059789 A1 | 3/2003 | Efimov et al. |
| 2003/0077608 A1 | 4/2003 | Coull et al. |
| 2003/0232355 A1 | 12/2003 | Norden et al. |
| 2004/0009479 A1 | 1/2004 | Wohlgemuth et al. |
| 2004/0058886 A1 | 3/2004 | Scaringe |
| 2004/0110296 A1 | 6/2004 | Vargeese et al. |
| 2004/0241855 A1 | 12/2004 | Cullis et al. |
| 2005/0053979 A1 | 3/2005 | Livak et al. |
| 2005/0075492 A1 | 4/2005 | Chen et al. |
| 2005/0209141 A1 | 9/2005 | Silver et al. |
| 2005/0222009 A1 | 10/2005 | Lamensdorf et al. |
| 2005/0233455 A1 | 10/2005 | Damha et al. |
| 2006/0111312 A1 | 5/2006 | Eshleman et al. |

(Continued)

FOREIGN PATENT DOCUMENTS

| | | |
|---|---|---|
| CN | 1860228 A | 11/2006 |
| CN | 101076592 A | 11/2007 |

(Continued)

OTHER PUBLICATIONS

Neilsen et al., IsomiRs—the overlooked repertoire in the dynamic microRNAome, Trends in Genetics, vol. 28, pp. 544-549. (Year: 2012).*
Li et al., miRNA arm selection and isomiR distribution in gastric cancer, BMC Genomics, vol. 13, supplement 1, S13, pp. 1-10. (Year: 2012).*
Cifuentes et al., A novel miRNA processing pathway independent of Dicer requires Argonaute2 catalytic activity, Sciencexpress, vol. 10.1126, pp. 1-4. (Year: 2010).*
Wang et al., Predicting siRNA potency with random forests and support vector machines, BMC Genomics, vol. 11, supplement 3:S2, pp. 1-7. (Year: 2010).*
Chorn et al., Single-stranded microRNA mimics, RNA, vol. 18, pp. 1796-1804. (Year: 2012).*

(Continued)

*Primary Examiner* — Dana H Shin
(74) *Attorney, Agent, or Firm* — Leydig, Voit & Mayer, Ltd.

(57) ABSTRACT

The invention provides an artificial match-type miRNA utilizing miRNA. In particular, the invention provides a single strand nucleic acid containing an X region and a Y region, wherein the 3'-terminal of the X region and the 5'-terminal of the Y region are linked via a linker region of a non-nucleotide structure, the X region contains a guide strand sequence of a mature miRNA, and the Y region contains a sequence completely complementary to the X region is an artificial match-type miRNA. The artificial match-type miRNA can suppress expression of the target gene.

9 Claims, 7 Drawing Sheets

Specification includes a Sequence Listing.

(56) References Cited

U.S. PATENT DOCUMENTS

| | | |
|---|---|---|
| 2006/0130176 A1 | 6/2006 | Reyes-Taboada et al. |
| 2006/0276421 A1 | 12/2006 | Kunugiza et al. |
| 2007/0037167 A1 | 2/2007 | Wohlgemuth et al. |
| 2007/0244058 A1 | 10/2007 | Ohgi et al. |
| 2007/0270365 A1 | 11/2007 | Jimenez et al. |
| 2008/0032918 A1 | 2/2008 | Silver et al. |
| 2008/0050744 A1 | 2/2008 | Brown et al. |
| 2008/0199853 A1 | 8/2008 | Wohlgemuth et al. |
| 2009/0005332 A1 | 1/2009 | Hauser et al. |
| 2009/0081274 A1 | 3/2009 | Silver et al. |
| 2009/0123501 A1 | 5/2009 | Levitt et al. |
| 2009/0130751 A1 | 5/2009 | Davidson et al. |
| 2009/0176723 A1 | 7/2009 | Brown et al. |
| 2009/0239814 A1 | 9/2009 | Manoharan et al. |
| 2009/0263796 A1 | 10/2009 | Wohlgemuth et al. |
| 2009/0292005 A1 | 11/2009 | Ohgi et al. |
| 2010/0009377 A1 | 1/2010 | Wohlgemuth et al. |
| 2010/0137407 A1 | 6/2010 | Abe et al. |
| 2010/0221266 A1 | 9/2010 | Gregory et al. |
| 2010/0292310 A1 | 11/2010 | Kelley et al. |
| 2010/0317714 A1 | 12/2010 | Xi et al. |
| 2011/0034545 A1 | 2/2011 | Kubo et al. |
| 2011/0052666 A1 | 3/2011 | Kaemmerer et al. |
| 2011/0055965 A1 | 3/2011 | Abe et al. |
| 2011/0064792 A1 | 3/2011 | Humphries et al. |
| 2011/0070584 A1 | 3/2011 | Wohlgemuth et al. |
| 2011/0159586 A1 | 6/2011 | Hauser |
| 2011/0190142 A1 | 8/2011 | Funke-Kaiser et al. |
| 2011/0200582 A1 | 8/2011 | Baryza et al. |
| 2011/0262914 A1 | 10/2011 | Wohlgemuth et al. |
| 2012/0004280 A1 | 1/2012 | Jadhav et al. |
| 2012/0010271 A1 | 1/2012 | Ohgi et al. |
| 2012/0021516 A1 | 1/2012 | Hannon et al. |
| 2012/0035246 A1 | 2/2012 | Ohgi et al. |
| 2012/0135521 A1 | 5/2012 | Eshleman et al. |
| 2012/0184598 A1 | 7/2012 | Hauser |
| 2013/0017223 A1 | 1/2013 | Hope et al. |
| 2013/0178514 A1* | 7/2013 | Deshmukh ......... A61K 31/7105 514/44 A |
| 2013/0179999 A1 | 7/2013 | Hannon et al. |
| 2013/0190494 A1 | 7/2013 | Carson et al. |
| 2013/0225652 A1 | 8/2013 | Chorn et al. |
| 2013/0253038 A1 | 9/2013 | Koizumi et al. |
| 2014/0171486 A1 | 6/2014 | Ohgi et al. |
| 2014/0171633 A1 | 6/2014 | Ohgi et al. |
| 2014/0329886 A1 | 11/2014 | Ohgi et al. |
| 2015/0073124 A1 | 3/2015 | Ohgi et al. |
| 2015/0105443 A1 | 4/2015 | Ohgi et al. |
| 2016/0319282 A1 | 11/2016 | Kuroda et al. |
| 2017/0037398 A1 | 2/2017 | Kuroda et al. |
| 2017/0088837 A1 | 3/2017 | Singer et al. |
| 2017/0306325 A1 | 10/2017 | Ohgi et al. |
| 2018/0119151 A1 | 5/2018 | Aoki et al. |
| 2018/0326091 A1 | 11/2018 | Aoki et al. |
| 2019/0010503 A1 | 1/2019 | Ishida et al. |
| 2019/0270707 A1 | 9/2019 | Baiocchi et al. |

FOREIGN PATENT DOCUMENTS

| | | |
|---|---|---|
| CN | 101121934 A | 2/2008 |
| CN | 101679962 A | 3/2010 |
| CN | 101981185 A | 2/2011 |
| CN | 101845071 B | 2/2012 |
| CN | 102559666 A | 7/2012 |
| CN | 102784398 A | 11/2012 |
| CN | 103052711 A | 4/2013 |
| CN | 103221549 A | 7/2013 |
| CN | 103370416 A | 10/2013 |
| DE | 873543 C | 4/1953 |
| EP | 1013770 A1 | 6/2000 |
| EP | 1669450 A1 | 6/2006 |
| EP | 2143792 A1 | 1/2010 |
| EP | 2233573 A1 | 9/2010 |
| EP | 2256191 A1 | 12/2010 |
| EP | 2302055 A1 | 3/2011 |
| EP | 1669450 B1 | 11/2011 |
| EP | 2431466 A1 | 3/2012 |
| EP | 2436767 A1 | 4/2012 |
| EP | 2527440 A1 | 11/2012 |
| EP | 2562257 A1 | 2/2013 |
| EP | 2647713 A1 | 10/2013 |
| EP | 2801617 A1 | 11/2014 |
| JP | 2004-524032 A | 8/2004 |
| JP | 2005-508634 A | 4/2005 |
| JP | 2005-521393 A | 7/2005 |
| JP | 2007-508030 A | 4/2007 |
| JP | 2007-516695 A | 6/2007 |
| JP | 2008-510786 A | 4/2008 |
| JP | 2008-519606 A | 6/2008 |
| JP | 2008-526213 A | 7/2008 |
| JP | 2008-220366 A | 9/2008 |
| JP | 2008-239596 A | 10/2008 |
| JP | 2008-278784 A | 11/2008 |
| JP | 2010-104368 A | 5/2010 |
| JP | 2010-527616 A | 8/2010 |
| JP | 2011-501662 A | 1/2011 |
| JP | 2011-504730 A | 2/2011 |
| JP | 2011-220969 A | 11/2011 |
| JP | 2013-055913 A | 3/2013 |
| JP | 2013-153736 A | 8/2013 |
| RU | 2410430 C2 | 1/2011 |
| WO | WO 1995/029241 A2 | 11/1995 |
| WO | WO 1998/016550 A1 | 4/1998 |
| WO | WO 2003/068798 A1 | 8/2003 |
| WO | WO 2003/079757 A2 | 10/2003 |
| WO | WO 2004/015075 A2 | 2/2004 |
| WO | WO 2004/015107 A2 | 2/2004 |
| WO | WO 2004/058886 A1 | 7/2004 |
| WO | WO 2004/090108 A2 | 10/2004 |
| WO | WO 2005/019453 A2 | 3/2005 |
| WO | WO 2005/030960 A1 | 4/2005 |
| WO | WO 2005/037317 A2 | 4/2005 |
| WO | WO 2006/022325 A1 | 3/2006 |
| WO | WO 2006/024880 A2 | 3/2006 |
| WO | WO 2006/074108 A2 | 7/2006 |
| WO | WO 2006/088490 A2 | 8/2006 |
| WO | WO 2006/137941 A2 | 12/2006 |
| WO | WO 2007/099981 A1 | 9/2007 |
| WO | WO 2007/131237 A2 | 11/2007 |
| WO | WO 2008/116094 A2 | 9/2008 |
| WO | WO 2008/137862 A2 | 11/2008 |
| WO | WO 2008/137867 A2 | 11/2008 |
| WO | WO 2008/140126 A1 | 11/2008 |
| WO | WO 2008/147839 A1 | 12/2008 |
| WO | WO 2009/000520 A1 | 12/2008 |
| WO | WO 2009/029690 A1 | 3/2009 |
| WO | WO 2009/054551 A2 | 4/2009 |
| WO | WO 2009/065022 A2 | 5/2009 |
| WO | WO 2009/073809 A2 | 6/2009 |
| WO | WO 2009/076321 A2 | 6/2009 |
| WO | WO 2009/102081 A1 | 8/2009 |
| WO | WO 2009/126563 A1 | 10/2009 |
| WO | WO 2009/143619 A1 | 12/2009 |
| WO | WO 2010/056737 A2 | 5/2010 |
| WO | WO 2010/058824 A1 | 5/2010 |
| WO | WO 2011/008730 A2 | 1/2011 |
| WO | WO 2011/009624 A1 | 1/2011 |
| WO | WO 2011/076807 A2 | 6/2011 |
| WO | WO 2011/119887 A1 | 9/2011 |
| WO | WO 2011/132672 A1 | 10/2011 |
| WO | WO 2011/133889 A1 | 10/2011 |
| WO | WO 2012/005368 A1 | 1/2012 |
| WO | WO 2012/012676 A2 | 1/2012 |
| WO | WO 2012/017919 A1 | 2/2012 |
| WO | WO 2012/030683 A2 | 3/2012 |
| WO | WO 2011/055888 A1 | 5/2012 |
| WO | WO 2012/074038 A1 | 6/2012 |
| WO | WO 2012/106591 A1 | 8/2012 |
| WO | WO 2012/161124 A1 | 11/2012 |
| WO | WO 2013/077446 A1 | 5/2013 |
| WO | WO 2013/103146 A1 | 7/2013 |
| WO | WO 2003/072745 A2 | 9/2013 |
| WO | WO 2013/133221 A1 | 9/2013 |

(56) References Cited

FOREIGN PATENT DOCUMENTS

| WO | WO 2013/166155 A1 | 11/2013 |
|---|---|---|
| WO | WO 2013/180038 A1 | 12/2013 |
| WO | WO 2014/190157 A1 | 11/2014 |
| WO | WO 2015/093495 A1 | 6/2015 |
| WO | WO 2015/099188 A1 | 7/2015 |

OTHER PUBLICATIONS

Deiters, Alexander, "Small Molecule Modifiers of the microRNA and RNA Interference Pathway," *The AAPS Journal*, 12(1): 51-60 (Mar. 2010).

Takeshita et al., "Systemic Delivery of Synthetic MicroRNA-16 Inhibits the Growth of Metastatic Prostate Tumors via Downregulation of Multiple Cell-cycle Genes," *Molecular Therapy*, 18(1): 181-187 (Jan. 2010).

Japanese Patent Office, International Search Report in International Patent Application No. PCT/JP2014/084724 (dated Mar. 24, 2015).

Cifuentes et al., "A Novel miRNA Processing Pathway Independent of Dicer Requires Argonaute2 Catalytic Activity," *Science*, 328(5986): 1694-1698 (2010).

Cheloufi et al., "A Dicer-independent miRNA biogenesis pathway that requires Ago catalysis," *Nature*, 465(7298): 584-589 (2010).

Ge et al., "Minimal-length short hairpin RNAs: The relationship of structure and RNAi activity," *RNA*, 16(1): 106-117 (2010).

Guennewig et al., "Synthetic pre-microRNAs reveal dual-strand activity of miR-34a on TNF-α," *RNA*, 20(1): 61-75 (2013).

Johnson et al., "Somatic activation of the K-ras oncogene causes early onset lung cancer in mice," *Nature*, 410(6832): 1111-1116 (2001).

Ma et al., "Designing Ago2-specific siRNA/shRNA to Avoid Competition with Endogenous miRNAs," *Mol. Ther. Nucleic Acids*, 3: e176 (2014).

McManus et al., "Gene silencing using micro-RNA designed hairpins," *RNA*, 8(6): 842-850 (2002).

Michlewski et al., "Posttranscriptional Regulation of miRNAs Harboring Conserved Terminal Loops," *Mol. Cell*, 32(3): 383-393 (2008).

Myburgh et al., "Optimization of Critical Hairpin Features Allows miRNA-based Gene Knockdown Upon Single-copy Transduction," *Mol. Ther.—Nucleic Acids*, 3: e207 (2014).

Winter et al., "Loop-miRs: active microRNAs generated from single-stranded loop regions," *Nucleic Acids Res.*, 41(10): 5503-5512 (2013).

Wu et al., "Improved siRNA/shRNA Functionality by Mismatched Duplex," *PLoS One*, 6(12): e28580 (2011).

Yang et al., "Conserved vertebrate *mir-451* provides a platform for Dicer-independent, Ago2-mediated microRNA biogenesis," *Proc. Natl. Acad. Sci. U.S.A.*, 107(34): 15163-15168 (2010).

Yang et al., "Functional parameters of Dicer-independent microRNA biogenesis," *RNA*, 18(5): 945-957 (2012).

Zeng et al., "Structural requirements for pre-microRNA binding and nuclear export by Exportin 5," *Nucleic Acids Res.*, 32(16): 4776-4785 (2004).

European Patent Office, Extended European Search Report in European Patent Application No. 14873783.6 (dated Jul. 11, 2017).

Abe et al., "Dumbbell-Shaped Nanocircular RNAs for RNA Interference," *J. Am. Chem. Soc.*, 129(49): 15108-15109 (2007).

Anderson et al., "Bispecific Short Hairpin siRNA Constructs Targeted to CD4, CXCR4, and Ccr5 Confer HIV-1 Resistance," *Oligonucleotides*, 13(5): 303-312 (2003).

Bosi et al., "Antimycobacterial Activity of Ionic Fullerene Derivatives," *Bioorg. Med. Chem. Lett.*, 10(10): 1043-1045 (2000).

Cheng et al., "TGF-β1 Gene Silencing for Treating Liver Fibrosis," *Mol. Pharm.*, 6(3): 772-779 (2009).

Confalone et al., "Design and Synthesis of Potential DNA Cross-Linking Reagents Based on the Anthramycin Class of Minor Groove Binding Compounds," *J. Org. Chem.*, 53(3): 482-487 (1988).

GENBANK, "*Homo sapiens* periostin, osteoblast specific factor (POSTN), transcript variant 1, mRNA," Accession No. NM_006475.2 (2008).

Kumar et al., "Pyrrolidine Nucleic Acids: DNA/PNA Oligomers with 2-Hydroxy/Aminomethyl-4-(thymin-1-yl)pyrrolidine-N-acetic acid," *Org. Lett.*, 3(9): 1269-1272 (2001).

Leirdal et al., "Gene silencing in mammalian cells by preformed small RNA duplexes," *Biochem. Biophys. Res. Commun.*, 295(3): 744-748 (2002).

Lonkar et al., "Design and synthesis of conformationally frozen peptide nucleic acid backbone: chiral piperidine PNA as a hexitol nucleic acid surrogate," *Bioorg. Med. Chem. Lett.*, 14(9): 2147-2149 (2004).

Mcanuff et al., "Potency of siRNA *Versus* shRNA Mediated Knockdown *In Vivo*," *J. Pharm. Sci.*, 96(11): 2922-2930 (2007).

Nilsson et al., "Padlock probes: Circularizing Oligonucleotides for Localized DNA Detection," *Science*, 265(5181): 2085-2088 (1994).

Oliveira et al., "Efficient and Expeditious Protocols for the Synthesis of Racemic and Enantiomerically Pure Endocyclic Enecarbamates from N-Acetyl Lactams and N-Acyl Pyrrolidines," *J. Org. Chem.*, 64(18): 6646-6652 (1999).

Püschl et al., "Pyrrolidine PNA: A Novel Conformationally Restricted PNA Analogue," *Org. Lett.*, 2(26): 4161-4163 (2000).

Watanabe et al., "PERIOSTIN regulates MMP-2 expression via the αvβ3 integrin/ERK pathway in human periodontal ligament cells," *Archives of Oral Biology*, 57(1): 52-59 (2012).

Webster et al., "Comparison of Solution-Phase and Solid-Phase Syntheses of a Restrained Proline-Containing Analogue of the Nodularin Macrocycle," *Tetrahedron Lett.*, 38(32): 5713-5716 (1997).

Wu, "Improved siRNA/shRNA Functionality by Mismatched Duplex," *PLoS One*, 6(12): e28580 (2011).

Yamakawa et al. "Properties and Anti-HIV Activity of Nicked Dumbbell Oligonucleotides," *Nucleosides & Nucleotides*, 15(1-3): 519-529 (1996).

Australian Patent Office, Patent Examination Report No. 1 in Australian Patent Application No. 2011274854 (dated Oct. 24, 2014).

Chinese Patent Office, Office Action and Search Report in Chinese Patent Application No. 201480070373.4 (dated Mar. 30, 2018).

European Patent Office, Supplementary European Search Report in European Patent Application No. 11748250.5 (dated Apr. 5, 2012).

U.S. Patent and Trademark Office, Supplemental Structure Search Results (ACS on STN) Referring to WO 2009/000520, HCAPLUS Accession No. 2009: 1297, Document No. 150: 95775, in U.S. Appl. No. 13/254,159 (dated Nov. 9, 2012).

Yin et al., "HAS-miR-34a as a molecular marker for early diagnosis of renal cell carcinoma," *Modern Oncology*, 20(7): 1398-1401 (2012).

Chen et al., "The hsa-let-7a miRNA Enhances Ara-C Induced Apoptosis in Human Acute Myeloid Leukemia Cells," *Clinical Lymphoma, Myeloma & Leukemia*, 13 (Supplement 2): S368, Abstract 203 (Sep. 2013).

Chinese Patent Office, The First Office Action in Chinese Patent Application No. 201480076467.2 (dated Jul. 25, 2018).

European Patent Office, Communication Pursuant to Article 94(3) EPC in European Patent Application No. 14873783.6 (dated Sep. 10, 2018).

Japanese Patent Office, Notification of Reasons for Refusal in Japanese Patent Application No. 2015-555042 (dated Dec. 4, 2018).

Baumann et al., "miRNA-based therapies: strategies and delivery platforms for oligonucleotide and non-oligonucleotide agents," *Future Med. Chem.*, 6(17): 1967-1984 (2014).

Jeong et al., "siRNA Conjugate Delivery Systems," *Bioconjug. Chem.*, 20(1): 5-14 (2009).

Kitamatsu et al., "Carrier PNA for shRNA delivery into cells," *Bioorg. Med. Chem. Lett.*, 19(13): 3410-3413 (2009).

Mäkilä et al., "Synthesis of multi-galactose-conjugated 2'-O-methyl oligoribonucleotides and their in vivo imaging with positron emission tomography," *Bioorg. Med. Chem.*, 22(24): 6806-6813 (2014).

Nitin et al., "Peptide-linked molecular beacons for efficient delivery and rapid mRNA detection in living cells," *Nucleic Acids Res.*, 32(6): e58 (2004).

(56) References Cited

OTHER PUBLICATIONS

Nitin et al., "NLS Peptide Conjugated Molecular Beacons for Visualizing Nuclear RNA in Living Cells," *Bioconjug. Chem.*, 19(11): 2205-2211 (2008).
Seo et al., "Cholesterol-Linked Fluorescent Molecular Beacons with Enhanced Cell Permeability," *Bioconjug. Chem.*, 17(5): 1151-1155 (2006).
Shim et al., "Efficient and targeted delivery of siRNA *in vivo*," *FEBS J.*, 277(23): 4814-4827 (2010).
Takaoka, "Natural Immunity and Viral Infection" (2011) [obtained at http://www.igm.hokudai.ac.jp/sci/files/innate_virus.pdf on Sep. 19, 2018].
Trang et al., "Systemic Delivery of Tumor Suppressor microRNA Mimics Using a Neutral Lipid Emulsion Inhibits Lung Tumors in Mice," *Mol. Ther.*, 19(6): 1116-1122 (2011).
Upert et al., "Inhibition of HIV Replication by Cyclic and Hairpin PNAs Targeting the HIV-1 TAR RNA Loop," *J. Nucleic Acids*, 2012: 591025 (2012).
Zhu et al., "Targeted Delivery of siRNA to Hepatocytes and Hepatic Stellate Cells by Bioconjugation," *Bioconjug. Chem.*, 21(11): 2119-2127 (2010).
European Patent Office, Extended European Search Report in European Patent Application No. 16772690.0 (dated Jan. 18, 2019).
Japanese Patent Office, International Search Report in International Patent Application No. PCT/JP2015/086378 (dated Mar. 15, 2016).
Japanese Patent Office, International Search Report in International Patent Application No. PCT/JP2016/059779 (dated Jun. 7, 2016).
Japanese Patent Office, Notice of Reasons for Refusal in Japanese Patent Application No. 2016-566558 (dated Oct. 2, 2018).
Schmitter et al., "Effects of Dicer and Argonaute down-regulation on mRNA levels in human HEK293 cells," *Nucleic Acids Res.*, 34(17): 4801-4815 (2006).
Völler et al., "Strong reduction of AGO2 expression in melanoma and cellular consequences," *Br. J. Cancer*, 109(12): 3116-3124 (2013).
Abe et al., "Specific inhibition of influenza virus RNA polymerase and nucleoprotein gene expression by circular dumbbell RNA/DNA chimeric oligonucleotides containing antisense phosphodiester oligonucleotides," *FEBS Lett.*, 425(1): 91-96 (1998).
Abe et al., "Synthesis, Structure, and Biological Activity of Dumbbell-Shaped Nanocircular RNAs for RNA Interference," *Bioconjug. Chem.*, 22(10): 2082-2092 (2011).
Bailén et al., "Direct synthesis of hydroxamates from carboxylic acids using 2-mercaptopyridone-1-oxide-based thiouronium salts," *Tetrahedron Letters*, 42(30): 5013-5016 (2001).
Bradshaw et al., "A Simple and Convenient Method for the Preparation of N,N'-Dibenzyldiaza-crown Compounds," *Journal of Organic Chemistry*, 53(8): 1808-1810 (1988).
Bramsen et al., "Improved silencing properties using small internally segmented interfering RNAs," *Nucleic Acids Res.*, 35(17): 5886-5897 (2007).
Clusel et al., "*Ex vivo* regulation of specific gene expression by nanomolar concentration of double-stranded dumbbell oligonucleotides," *Nucleic Acids Res.*, 21(15): 3405-3411 (1993).
Collins et al., "The Schistosomicidal and Toxic Effects on Some αω-DI(p-aminophenoxy)alkanes and Related Monoamines," *Br. J. Pharmacol. Chemother.*, 13(3): 238-243 (1958).
Dankwardt, "Solid Phase Synthesis of Hydroxamic Acids," *Synlett*, 1998(7): 761 (Jul. 1998).
De La Torre et al., "Synthesis of Oligonucleotides Carrying Anchoring Groups and Their Use in the Preparation of Oligonucleotide-Gold Conjugates," *Helvetica Chimica Acta*, 85: 2594-2607 (2002).
Elbashir et al., "Functional anatomy of siRNAs for mediating efficient RNAi in *Drosophila melanogaster* embryo lysate," *EMBO J.*, 20(23): 6877-6888 (2001).
Fire et al., "Potent and specific genetic interference by double-stranded RNA in *Caenorhabditis elegans*," *Nature*, 391: 806-811 (1998).

Gatto et al., "Syntheses and Binding Properties of Bibracchial Lariat Ethers (BiBLEs): Survey of Synthetic Methods and Cation Selectivities," *J. Org. Chem.*, 51(26): 5373-5384 (1986).
Graubaum et al., "New Cryptands with 1,3,5-Triazines as Ring Building Blocks," *J. Prakt. Chem.*, 337(1): 534-537 (1995).
Hamazaki et al., "Inhibition of Influenza Virus Replication in MDCK Cells by Circular Dumbbell RNA/DNA Chimeras with Closed Alkyl Loop Structures," *Helvetica Chimica Acta*, 85(7): 2183-2194 (2002).
Hoogerhout et al., "Synthesis of fragments of the capsular polysaccharide of *haemophilus influenzae* type B, comprising two or three repeating units," *Tetrahedron Letters*, 28(14): 1553-1556 (1987).
Hosoya et al., "Sequence-specific inhibition of a transcription factor by circular dumbbell DNA oligonucleotides," *FEBS Lett.*, 461(3): 136-140 (1999).
Ihara et al., "Enantioselective ester hydrolysis by hydroxamic acids of N-benzyloxycarbonyl-L-amino acids or optically active amines in cetyltrimethylammonium bromide," *Journal of Organic Chemistry*, 45(9): 1623-1625 (1980).
Jakobsen et al., "Polyaza crown ethers as nonnucleosidic building blocks in DNA-conjugates," 234th American Chemical Society (ACS) National Meeting, Abstract BIOL-071 (Aug. 19, 2007).
Kunugiza et al., "Inhibitory effect of ribbon-type NF-κB decoy oligodeoxynucleotides on osteoclast induction and activity *in vitro* and *in vivo*," *Arthritis Res. Ther.*, 8(4): R103 (2006).
Limbach et al., "Summary: the modified nucleosides of RNA," *Nucleic Acids Res.*, 22(12): 2183-2196 (1994).
Liu et al., "Enhanced proliferation, invasion, and epithelial-mesenchymal transition of nicotine-promoted gastric cancer by periostin," *World J. Gastroenterol.*, 17(21): 2674-2680 (2011).
Liu et al., "Membrane Anchored Immunostimulatory Oligonucleotides for in Vivo Cell Modification and Localized Immunotherapy," *Angewandte Chemie, International Edition*, 50(31): 7052-7055 and supporting information (2011).
Maeda et al., "Synthesis of N-Unsubstituted Di- and Triaza Crown Ethers," *Bulletin of the Chemical Society of Japan*, 56(10): 3073-3077 (1983).
Nykanen et al., "ATP Requirements and Small Interfering RNA Structure in the RNA Interference Pathway," *Cell*, 107(3): 309-321 (2001).
Paddison et al., "Short hairpin RNAs (shRNAs) induce sequence-specific silencing in mammalian cells," *Genes Dev.*, 16(8): 948-958 (2002).
Sommer et al., "Synthesis of Potentially Cytoactive Amino Acid Amide Mustards," *Journal of Medicinal Chemistry*, 9(1): 84-88 (1966).
Sonoke et al., "Tumor Regression in Mice by Delivery of Bcl-2 Small Interfering RNA with Pegylated Cationic Liposomes," *Cancer Research*, 68(21): 8843-8851 (Nov. 1, 2008).
Teramoto et al., "Prediction of siRNA functionality using generalized string kernel and support vector machine," *FEBS Lett.*, 579(13): 2878-2882 (2005).
Yoshida et al., "Increased Expression of Periostin in Vitreous and Fibrovascular Membranes Obtained from Patients with Proliferative Diabetic Retinopathy," *Investigative Ophthalmology & Visual Science*, 52(8): 5670-5678 (2011).
Yu et al., "RNA interference by expression of short-interfering RNAs and hairpin RNAs in mammalian cells," *Proc. Natl. Acad. Sci. USA*, 99(9): 6047-6052 (2002).
Chinese Patent Office, Notification of the Second Office Action in Chinese Patent Application No. 201380028696.2 (dated Jul. 18, 2016).
European Patent Office, Supplementary European Search Report in European Patent Application No. 11746147.5 (dated Mar. 26, 2012).
European Patent Office, Communication Pursuant to Article 94(3) EPC in European Patent Application No. 11746147.5 (dated Apr. 20, 2012).
European Patent Office, Communication Pursuant to Article 94(3) EPC in European Patent Application No. 11746147.5 (dated Sep. 26, 2012).
European Patent Office, Communication Pursuant to Article 94(3) EPC in European Patent Application No. 11746147.5 (dated Mar. 25, 2013).

(56) References Cited

OTHER PUBLICATIONS

European Patent Office, Communication Pursuant to Article 94(3) EPC in European Patent Application No. 11748250.5 (dated May 29, 2012).
European Patent Office, Supplementary European Search Report in European Patent Application No. 12864101.6 (dated Sep. 1, 2015).
European Patent Office, Extended European Search Report in European Patent Application No. 13184178.5 (dated Oct. 25, 2013).
European Patent Office, Extended European Search Report in European Patent Application No. 15169933.7 (dated Jul. 29, 2015).
European Patent Office, Communication Pursuant to Rule 164(1) EPC in European Patent Application No. 13167541.5 (dated Jul. 31, 2013).
European Patent Office, Communication Pursuant to Rule 164(1) EPC in European Patent Application No. 13797956.3 (dated Jan. 4, 2016).
Japanese Patent Office, International Search Report in International Patent Application No. PCT/JP2012/080461 (dated Jan. 22, 2013).
Japanese Patent Office, International Search Report in International Patent Application No. PCT/JP2012/084247 (dated Apr. 16, 2013).
Japanese Patent Office, International Search Report in International Patent Application No. PCT/JP2013/059494 (dated Jun. 4, 2013).
Japanese Patent Office, International Search Report in International Patent Application No. PCT/JP2013/064541 (dated Jul. 2, 2013).
Japanese Patent Office, Notice of Reasons for Refusal in Japanese Patent Application No. 2014-518427 (dated May 17, 2016).
United States Patent and Trademark Office, Office Action in U.S. Appl. No. 13/254,159 (dated Nov. 21, 2012).
United States Patent and Trademark Office, Office Action in U.S. Appl. No. 14/135,468 (dated May 8, 2015).
Batenburg et al., "Combined Renin Inhibition/(Pro)Renin Receptor Blockade in Diabetic Retinopathy—A Study in Transgenic (mREN2)27 Rats," *PLoS One*, 9(6): e100954 (2014).
Danser et al., "Renin, Prorenin, and Immunoreactive Renin in Vitreous Fluid from Eyes With and Without Diabetic Retinopathy," *J. Clin. Endocrinol. Metabol.*, 68(1): 160-167 (1989).
Genbank, "*Homo sapiens* glyceraldehyde-3-phosphate dehydrogenase (GADPH), transcript variant 1, mRNA," Accession No. NM_002046 (2014) [obtained at www.ncbi.nlm.nih.gov on Oct. 7, 2019].
Genbank, "*Homo sapiens* ATPase H+ transporting accessory protein 2 (ATP6AP2), mRNA.," Accession No. NM_005765 (2019) [obtained at www.ncbi.nlm.nih.gov on Oct. 7, 2019].
Hamasaki et al., "Efficacy of a Novel Class of RNA Interference Therapeutic Agents," *PLoS One*, 7(8): e42655 (2012).
Kanda et al., "(Pro)renin receptor is associated with angiogenic activity in proliferative diabetic retinopathy," *Diabetologia*, 55: 3104-3443 (2012).
Kanda, "(Pro)renin Receptor in the Pathogenesis of Proliferative Diabetic Retinopathy," *Jpn. J. Ophthalmol.*, 118(11): 916-926 (2014).
Satofuka et al., "Suppression of Ocular Inflammation in Endotoxin-Induced Uveitis by Inhibiting Nonproteolytic Activation of Prorenin," *Invest. Ophthalmol. Vis. Sci.*, 47(6): 2686-2692 (2006).
Zuyeva et al., "Changes of retinal neurons and Muller glial cells in patients with type II diabetes in treatment of diabetic retinopathy with angiotensin-converting enzyme inhibitor," *Vestnik Oftamologii*, 129(3): 44-47 (2013).
European Patent Office, Extended European Search Report in European Patent Application No. 16881846 (dated Apr. 16, 2019).
Japanese Patent Office, International Search Report in International Patent Application No. PCT/JP2016/089216 (dated Mar. 28, 2017).
Russian Patent Office, Office Action and Search Report in Russian Patent Application No. 2018127481 (dated Mar. 27, 2019).
Ming et al., "The Tumor Research Frontiers," *Fourth Military Medical University Press*, 10 (Chinese Edition): 25 (2010).
She et al., "Organic and Biochemistry," *China Forestry Publishing House*, 3rd Edition (Chinese Edition), p. 280 (2009).
China National Intellectual Property Office, Office Action and Search Report in Chinese Patent Application No. 201480070373.4 (dated Mar. 30, 2018).
China National Intellectual Property Office, Office Action and Search Report in Chinese Patent Application No. 201180027223.1 (dated Nov. 21, 2013).
China National Intellectual Property Office, Office Action and Search Report in Chinese Patent Application No. 201180037592.9 (dated Sep. 23, 2014).
Genbank, "*Homo sapiens* catenin (cadherin-associated protein), beta 1, 88kDa (CTNNB1), transcript variant 1, mRNA," Accession No. NM_001904.3 (2010) [obtained at https://www.ncbi.nlm.nih.gov/nuccore/148228165?sat=14&satkey=4105514].
Ivashchenko et al., "Specific Features of System Silencing of Homologous Sequences in the Course of RNA Interference," *Uspekhi Sovremennoj Biologii*, 129(5): 419-439 (2009).
Müller (editor), *Nucleic Acids from A to Z: A Concise Encyclopedia*, entry for "micro-Rna (miRNA)," p. 197 (2008).
China National Intellectual Property Office, The Second Office Action in Chinese Patent Application No. 201480076467.2 (dated Jun. 5, 2019).
Japanese Patent Office, Office Action in Japanese Patent Application No. 2018-113017 (dated Jun. 11, 2019).
Japanese Patent Office, Office Action in Japanese Patent Application No. 2017-509942 (dated Jul. 2, 2019).
Russian Federal Service for Intellectual Property, Office Action in Russian Patent Application No. 2017126566 (dated Jun. 6, 2019).
U.S. Appl. No. 13/254,150, filed Aug. 31, 2011.
U.S. Appl. No. 13/254,159, filed Aug. 31, 2011.
U.S. Appl. No. 14/134,704, filed Dec. 19, 2013.
U.S. Appl. No. 14/362,762, filed Jun. 4, 2014.
U.S. Appl. No. 14/403,259, filed Nov. 24, 2014.
U.S. Appl. No. 15/106,958, filed Jun. 21, 2016.
U.S. Appl. No. 15/496,143, filed Apr. 25, 2017.
U.S. Appl. No. 15/539,226, filed Jun. 23, 2017.
U.S. Appl. No. 15/562,231, filed Sep. 27, 2017.
U.S. Appl. No. 16/065,779, filed Jun. 22, 2018.
NCBI, "*Homo sapiens* renin (REN), mRNA," NCBI Reference Sequence No. NM_000537.4 (2019).
Tarantul et al., "Single-stranded DNA (ssDNA)," *Slovar biotekhnologicheskikh terminov* (Dictionary of Bioengineering Terms), publication page and entry page 478 (2009).

\* cited by examiner (A) AXL/GAPDH (B) MET/GAPDH

US 10,934,542 B2

SEQUENCE LISTING

<160> NUMBER OF SEQ ID NOS: 47

<210> SEQ ID NO 1
<211> LENGTH: 22
<212> TYPE: RNA
<213> ORGANISM: Artificial Sequence
<220> FEATURE:
<223> OTHER INFORMATION: Synthetic mature miRNA (hsa-miR-34a)

<400> SEQUENCE: 1
uggcaguguc uuagcugguu gu                                        22

```
<210> SEQ ID NO 2
<211> LENGTH: 22
<212> TYPE: RNA
<213> ORGANISM: Artificial Sequence
<220> FEATURE:
<223> OTHER INFORMATION: Synthetic mature miRNA (hsa-let-7a)

<400> SEQUENCE: 2
ugagguagua gguuguauag uu                                             22

<210> SEQ ID NO 3
<211> LENGTH: 22
<212> TYPE: RNA
<213> ORGANISM: Artificial Sequence
<220> FEATURE:
<223> OTHER INFORMATION: Synthetic mature miRNA (hsa-let-7f)

<400> SEQUENCE: 3
ugagguagua gauuguauag uu                                             22

<210> SEQ ID NO 4
<211> LENGTH: 22
<212> TYPE: RNA
<213> ORGANISM: Artificial Sequence
<220> FEATURE:
<223> OTHER INFORMATION: Synthetic mature miRNA (hsa-miR-150)

<400> SEQUENCE: 4
ucucccaacc cuuguaccag ug                                             22

<210> SEQ ID NO 5
<211> LENGTH: 23
<212> TYPE: RNA
<213> ORGANISM: Artificial Sequence
<220> FEATURE:
<223> OTHER INFORMATION: Synthetic mature miRNA (hsa-miR-29b)

<400> SEQUENCE: 5
uagcaccauu ugaaaucagu guu                                            23

<210> SEQ ID NO 6
<211> LENGTH: 22
<212> TYPE: RNA
<213> ORGANISM: Artificial Sequence
<220> FEATURE:
<223> OTHER INFORMATION: Synthetic passenger strand (mature miR-34a)

<400> SEQUENCE: 6
caaucagcaa guauacugcc cu                                             22

<210> SEQ ID NO 7
<211> LENGTH: 22
<212> TYPE: RNA
<213> ORGANISM: Artificial Sequence
<220> FEATURE:
<223> OTHER INFORMATION: Synthetic guide strand (mature miR-34a
      scramble)

<400> SEQUENCE: 7
uguaucguua ucgggucggu ug                                             22

<210> SEQ ID NO 8
<211> LENGTH: 22
<212> TYPE: RNA
<213> ORGANISM: Artificial Sequence
<220> FEATURE:
```

```
<223> OTHER INFORMATION: Synthetic passenger strand (mature miR-34a
      scramble)

<400> SEQUENCE: 8
caaccgaccc gauaacgaua ca                                                  22

<210> SEQ ID NO 9
<211> LENGTH: 52
<212> TYPE: RNA
<213> ORGANISM: Artificial Sequence
<220> FEATURE:
<223> OTHER INFORMATION: Synthetic oligonucleotide

<400> SEQUENCE: 9
uggcaguguc uuagcugguu guuccggaac aaccagcuaa gacacugcca ua                 52

<210> SEQ ID NO 10
<211> LENGTH: 52
<212> TYPE: RNA
<213> ORGANISM: Artificial Sequence
<220> FEATURE:
<223> OTHER INFORMATION: Synthetic oligonucleotide

<400> SEQUENCE: 10
uguaucguua ucgggucggu uguccggaca accgacccga uaacgauaca ua                 52

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
ctcaaccagg acgactccat                                                     20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
agaccgcttc actcaggaaa                                                     20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
caggcagtgc agcatgtagt                                                     20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tgtccaacaa agtcccatga                                                     20
```

<210> SEQ ID NO 15
<211> LENGTH: 19
<212> TYPE: DNA
<213> ORGANISM: Artificial Sequence
<220> FEATURE:
<223> OTHER INFORMATION: Synthetic primer

<400> SEQUENCE: 15
atggggaagg tgaaggtcg                                                    19

<210> SEQ ID NO 16
<211> LENGTH: 23
<212> TYPE: DNA
<213> ORGANISM: Artificial Sequence
<220> FEATURE:
<223> OTHER INFORMATION: Synthetic primer

<400> SEQUENCE: 16
gggtcattga tggcaacaat atc                                               23

<210> SEQ ID NO 17
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 17
uggcaguguc uuagcugguu guucgaacaa ccagcuaaga cacugccaua                  50

<210> SEQ ID NO 18
<211> LENGTH: 48
<212> TYPE: RNA
<213> ORGANISM: Artificial Sequence
<220> FEATURE:
<223> OTHER INFORMATION: Synthetic oligonucleotide

<400> SEQUENCE: 18
uggcaguguc uuagcugguu guuaacaacc agcuaagaca cugccaua                    48

<210> SEQ ID NO 19
<211> LENGTH: 46
<212> TYPE: RNA
<213> ORGANISM: Artificial Sequence
<220> FEATURE:
<223> OTHER INFORMATION: Synthetic oligonucleotide

<400> SEQUENCE: 19
uggcaguguc uuagcugguu guacaaccag cuaagacacu gccaua                      46

<210> SEQ ID NO 20
<211> LENGTH: 51
<212> TYPE: RNA
<213> ORGANISM: Artificial Sequence
<220> FEATURE:
<223> OTHER INFORMATION: Synthetic oligonucleotide

<400> SEQUENCE: 20
uggcaguguc uuagcugguu guccggaac aaccagcuaa gacacugcca u                 51

<210> SEQ ID NO 21
<211> LENGTH: 49
<212> TYPE: RNA
<213> ORGANISM: Artificial Sequence
<220> FEATURE:
<223> OTHER INFORMATION: Synthetic oligonucleotide

<400> SEQUENCE: 21
uggcaguguc uuagcugguu guucgaacaa ccagcuaaga cacugccau      49

<210> SEQ ID NO 22
<211> LENGTH: 47
<212> TYPE: RNA
<213> ORGANISM: Artificial Sequence
<220> FEATURE:
<223> OTHER INFORMATION: Synthetic oligonucleotide

<400> SEQUENCE: 22
uggcaguguc uuagcugguu guuaacaacc agcuaagaca cugccau        47

<210> SEQ ID NO 23
<211> LENGTH: 45
<212> TYPE: RNA
<213> ORGANISM: Artificial Sequence
<220> FEATURE:
<223> OTHER INFORMATION: Synthetic oligonucleotide

<400> SEQUENCE: 23
uggcaguguc uuagcugguu guacaaccag cuaagacacu gccau          45

<210> SEQ ID NO 24
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 24
uggcaguguc uuagcugguu guuccggaac aaccagcuaa gacacugcca     50

<210> SEQ ID NO 25
<211> LENGTH: 48
<212> TYPE: RNA
<213> ORGANISM: Artificial Sequence
<220> FEATURE:
<223> OTHER INFORMATION: Synthetic oligonucleotide

<400> SEQUENCE: 25
uggcaguguc uuagcugguu guucgaacaa ccagcuaaga cacugcca       48

<210> SEQ ID NO 26
<211> LENGTH: 46
<212> TYPE: RNA
<213> ORGANISM: Artificial Sequence
<220> FEATURE:
<223> OTHER INFORMATION: Synthetic oligonucleotide

<400> SEQUENCE: 26
uggcaguguc uuagcugguu guuaacaacc agcuaagaca cugcca         46

<210> SEQ ID NO 27
<211> LENGTH: 44
<212> TYPE: RNA
<213> ORGANISM: Artificial Sequence
<220> FEATURE:
<223> OTHER INFORMATION: Synthetic oligonucleotide

<400> SEQUENCE: 27
uggcaguguc uuagcugguu guacaaccag cuaagacacu gcca           44

<210> SEQ ID NO 28

```
<211> LENGTH: 46
<212> TYPE: RNA
<213> ORGANISM: Artificial Sequence
<220> FEATURE:
<223> OTHER INFORMATION: Synthetic oligonucleotid

<400> SEQUENCE: 28
uggcaguguc uuagcugguu guacaaccag cuaagacacu gccacu                    46

<210> SEQ ID NO 29
<211> LENGTH: 52
<212> TYPE: RNA
<213> ORGANISM: Artificial Sequence
<220> FEATURE:
<223> OTHER INFORMATION: Synthetic oligonucleotid

<400> SEQUENCE: 29
uggcaguguc uuagcugguu guuccggaac aaccagcuaa gacacugcca cu             52

<210> SEQ ID NO 30
<211> LENGTH: 56
<212> TYPE: RNA
<213> ORGANISM: Artificial Sequence
<220> FEATURE:
<223> OTHER INFORMATION: Synthetic oligonucleotide

<400> SEQUENCE: 30
uggcaguguc uuagcugguu guuccggccg gaacaaccag cuaagacacu gccacu         56

<210> SEQ ID NO 31
<211> LENGTH: 48
<212> TYPE: RNA
<213> ORGANISM: Artificial Sequence
<220> FEATURE:
<223> OTHER INFORMATION: Synthetic oligonucleotide

<400> SEQUENCE: 31
uacuauucga cacgcgaagu uccggaacuu cgcgugucga auaguauu                  48

<210> SEQ ID NO 32
<211> LENGTH: 64
<212> TYPE: RNA
<213> ORGANISM: Artificial Sequence
<220> FEATURE:
<223> OTHER INFORMATION: Synthetic oligonucleotide

<400> SEQUENCE: 32
uggcaguguc uuagcugguu guugugagca auaguaagga agcaaucagc aaguauacug     60
cccu                                                                  64

<210> SEQ ID NO 33
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 33
aaccagcuaa gacacugcca cu                                              22

<210> SEQ ID NO 34
<211> LENGTH: 22
<212> TYPE: RNA
<213> ORGANISM: Artificial Sequence
<220> FEATURE:
<223> OTHER INFORMATION: Synthetic oligonucleotide
```

```
<400> SEQUENCE: 34
cuauacaacc uacuaccuca uc                                              22

<210> SEQ ID NO 35
<211> LENGTH: 72
<212> TYPE: RNA
<213> ORGANISM: Artificial Sequence
<220> FEATURE:
<223> OTHER INFORMATION: Synthetic oligonucleotide

<400> SEQUENCE: 35
ugagguagua gguuguauag uuuuagggug acacccacca cugggagaua acuauacaau      60
cuacugucuu uc                                                         72

<210> SEQ ID NO 36
<211> LENGTH: 46
<212> TYPE: RNA
<213> ORGANISM: Artificial Sequence
<220> FEATURE:
<223> OTHER INFORMATION: Synthetic oligonucleotide

<400> SEQUENCE: 36
ugagguagua gguuguauag uuaacuauac aaccuacuac cucauc                    46

<210> SEQ ID NO 37
<211> LENGTH: 52
<212> TYPE: RNA
<213> ORGANISM: Artificial Sequence
<220> FEATURE:
<223> OTHER INFORMATION: Synthetic oligonucleotide

<400> SEQUENCE: 37
ugagguagua gguuguauag uuuccggaaa cuauacaacc uacuaccuca uc              52

<210> SEQ ID NO 38
<211> LENGTH: 56
<212> TYPE: RNA
<213> ORGANISM: Artificial Sequence
<220> FEATURE:
<223> OTHER INFORMATION: Synthetic oligonucleotide

<400> SEQUENCE: 38
ugagguagua gguuguauag uuuccggccg gaaacuauac aaccuacuac cucauc          56

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
gaagccactg gagaaaaacg                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
cttcggcaga ctcttgtgag                                                 20
```

```
<210> SEQ ID NO 41
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 41
cacugauuuc aaauggugcu aga                                          23

<210> SEQ ID NO 42
<211> LENGTH: 64
<212> TYPE: RNA
<213> ORGANISM: Artificial Sequence
<220> FEATURE:
<223> OTHER INFORMATION: Synthetic oligonucleotide

<400> SEQUENCE: 42
gcugguuuca uauggugguu uagauuuaaa uagugauugu cuagcaccau uugaaaucag   60
uguu                                                               64

<210> SEQ ID NO 43
<211> LENGTH: 48
<212> TYPE: RNA
<213> ORGANISM: Artificial Sequence
<220> FEATURE:
<223> OTHER INFORMATION: Synthetic oligonucleotide

<400> SEQUENCE: 43
uagcaccauu ugaaaucagu guuaacacug auuucaaaug gugcuaga               48

<210> SEQ ID NO 44
<211> LENGTH: 54
<212> TYPE: RNA
<213> ORGANISM: Artificial Sequence
<220> FEATURE:
<223> OTHER INFORMATION: Synthetic oligonucleotide

<400> SEQUENCE: 44
uagcaccauu ugaaaucagu guuuccggaa acacugauuu caaauggugc uaga        54

<210> SEQ ID NO 45
<211> LENGTH: 58
<212> TYPE: RNA
<213> ORGANISM: Artificial Sequence
<220> FEATURE:
<223> OTHER INFORMATION: Synthetic oligonucleotide

<400> SEQUENCE: 45
uagcaccauu ugaaaucagu guuccggcc ggaaacacug auuucaaaug gugcuaga     58

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
cccaaggaca agaggcatgt                                              20

<210> SEQ ID NO 47
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 47
ccgccatact cgaactggaa                                              20
```

ARTIFICIAL MATCH-TYPE MIRNA FOR CONTROLLING GENE EXPRESSION AND USE THEREFOR

CROSS-REFERENCE TO RELATED APPLICATIONS

This patent application is the U.S. national phase of International Patent Application No. PCT/JP2014/084724, filed Dec. 27, 2014, which claims the benefit of Japanese Patent Application No. 2013-273033, filed on Dec. 27, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 9,847 bytes ASCII (Text) file named "725812SequenceListing.txt," created Jun. 24, 2016.

TECHNICAL FIELD

The present invention relates to an artificial match-type miRNA that suppresses gene expression, and use thereof.

BACKGROUND ART

MicroRNA (miRNA) is known as a nucleic acid molecule that suppresses gene expression and has been reported to suppress transcription of a protein encoded by a gene via, for example, the following production process. That is, an miRNA transcription product (Pri-miRNA) having a cap structure on the 5'-terminal and poly(A) on the 3'-terminal is produced in the nucleus. The aforementioned Pri-miRNA is cleaved by RNase (Drosha) to produce a miRNA precursor (Pre-miRNA). The aforementioned Pre-miRNA forms a hairpin structure having a loop region and a stem region. The Pre-miRNA moves out from the nucleus and is degraded by RNase (Dicer) in the cytoplasm, and a double stranded miRNA (mature miRNA) having 1-4 bases of overhang on the 3'-terminal is cleaved out. One of the strands of the double stranded miRNA is called a guide strand and the other strand is called a passenger strand, and the aforementioned guide strand is bonded to a complex similar to RNA-induced Silencing Complex (RISC). This miRNA/RISC complex binds to the 3' untranslated region (3'UTR) of particular mRNA to suppress translation of protein from the aforementioned mRNA.

It has been clarified that miRNA is deeply involved in life phenomena such as differentiation, cell proliferation, apoptosis and the like and many diseases such as viral infections, cancer and the like (patent document 1, non-patent document 1, non-patent document 2). Therefrom its application in, particularly, the medical field has been expected.

DOCUMENT LIST

Patent Document patent document 1: WO 2010/056737 A2

Non-Patent Documents non-patent document 1: Deiters, 2009, The AAPS Journal, 12, 51-60
non-patent document 2: Takeshita etal., 2010, Mol. Ther., 18, 181-187

SUMMARY OF THE INVENTION

Problems to be Solved by the Invention

For application of the aforementioned miRNA, for example, a method including use of a double stranded mature miRNA and the like are available. However, this method requires, before application, annealing of two single strand nucleic acid molecules, which produces a possibility of developing autoimmunity by TLR3 and the like that recognize the double strand.

Therefore, an object of the present invention is to provide a new artificial match-type miRNA utilizing miRNA.

Means of Solving the Problems

To achieve the aforementioned object, the artificial match-type miRNA of the present invention is a single strand nucleic acid comprising X region and Y region, characterized in that the 3'-terminal of the aforementioned X region and the 5'-terminal of the aforementioned Y region are linked via a linker region of a non-nucleotide structure, the aforementioned X region comprises a guide strand sequence of a mature miRNA, and the aforementioned Y region comprises a sequence completely complementary to the aforementioned X region.

The composition of the present invention is a composition for inhibiting the expression of a gene, and characteristically contains the above-mentioned artificial match-type miRNA of the present invention.

The composition of the present invention is a pharmaceutical composition which characteristically contains the above-mentioned artificial match-type miRNA of the present invention.

The expression inhibiting method of the present invention is a method of inhibiting the expression of a target gene, which characteristically uses the above-mentioned artificial match-type miRNA of the present invention.

The method of treating a disease of the present invention includes a step of administering the above-mentioned artificial match-type miRNA of the present invention to a patient, wherein the aforementioned guide strand sequence in the above-mentioned artificial match-type miRNA is a guide strand sequence of a mature miRNA that suppresses expression of genes involved in the aforementioned diseases.

Effect of the Invention

The artificial match-type miRNA of the present invention can be synthesized easily at a low cost, and can suppress translation of protein encoded by the aforementioned genes.

DESCRIPTION OF EMBODIMENTS

Unless otherwise specified, the terms used in the present specification mean what is generally meant by them in the art.

(1) Artificial Match-Type miRNA

The artificial match-type miRNA of the present invention is, as mentioned above, a single strand nucleic acid comprising X region and Y region, characterized in that the 3'-terminal of the aforementioned X region and the 5'-terminal of the aforementioned Y region are linked via a linker region of a non-nucleotide structure, the aforementioned X region comprises a guide strand sequence of a mature miRNA, and the aforementioned Y region comprises a sequence completely complementary to the aforementioned X region.

The artificial match-type miRNA of the present invention can suppress, for example, expression of the target gene. Suppression of expression means, for example, suppression of the translation of the aforementioned target gene, that is, suppression of the translation of a protein encoded by the aforementioned target gene, more particularly, suppression of the translation of the aforementioned protein from mRNA of the aforementioned target gene. The aforementioned inhibition of the expression of the target gene can be verified by, for example, a decrease in the amount of a transcription product derived from the target gene; a decrease in the activity of the aforementioned transcription product; a decrease in the amount of a translation product generated from the aforementioned target gene; a decrease in the activity of the aforementioned translation product; or the like. The aforementioned proteins may be, for example, mature proteins, precursor proteins before being subjected to processing or post-translational modification.

Since the artificial match-type miRNA of the present invention is a single strand nucleic acid molecule, annealing of two single strands is not necessary unlike mature miRNA, and can be produced at a low cost. Furthermore, since the artificial match-type miRNA of the present invention is a single strand nucleic acid molecule, for example, it can avoid recognition by TLR3, RIG-I, MDA5 and the like involved in autoimmunity.

Figure 1:
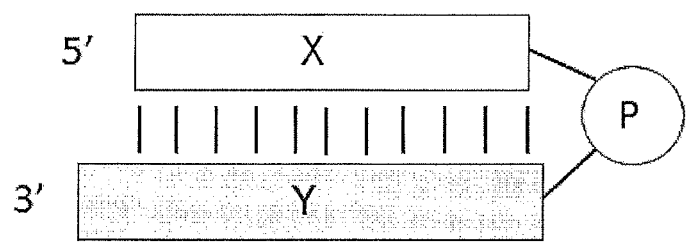
FIG. 1 is a schematic showing of one embodiment of the artificial match-type miRNA of the present invention.

An outline of the configurational relationship between the aforementioned X region and the aforementioned Y region in the artificial match-type miRNA of the present invention is shown in FIG. 1. FIG. 1 shows an outline and, for example, the length, shape and the like of each region are not limited. The artificial match-type miRNA of the present invention has, as shown in FIG. 1, the aforementioned X region on the 5'-side and the aforementioned Y region on the 3'-side, and the 3'-terminal of the aforementioned X region and the 5'-terminal of the aforementioned Y region are linked via linker region (shown with "P" in the Figure) of a non-nucleotide structure.

In the artificial match-type miRNA of the present invention, since the aforementioned Y region contains a sequence completely complementary to the aforementioned X region, the aforementioned X region and the aforementioned Y region are, for example, intramolecularly annealed. Intramolecular annealing is also referred to as, for example, self-annealing. The artificial match-type miRNA of the present invention is also said to form a double strand in the aforementioned intramolecularly-annealed region.

The artificial match-type miRNA of the present invention can also be referred to as a linear single strand nucleic acid molecule, wherein the 5'-terminal thereof and the 3'-terminal thereof are unlinked. To maintain the unbinding of the both termini, the 5'-terminal of the artificial match-type miRNA of the present invention is preferably, for example, a non-phosphoric acid group.

In the artificial match-type miRNA of the present invention, the aforementioned X region contains, as mentioned above, a guide strand sequence of a mature miRNA. The guide strand sequence of a mature miRNA is, for example, registered in various databases (e.g., www.mirbase.org/ etc.). Therefore, the aforementioned X region can be set based on, for example, the information of known mature miRNAs. The guide strand of the aforementioned mature miRNA is a strand, which is taken into an Argonaute (Ago) protein of RNA-induced silencing complex (RISC) and binds to mRNA of the target.

The aforementioned X region may consist solely of, for example, the aforementioned guide strand sequence, or may further have an additional sequence. In the latter case, the aforementioned X region consists of, for example, the aforementioned guide strand sequence and the aforementioned additional sequence, and the aforementioned additional sequence is linked to, for example, the 3'-terminal of the aforementioned guide strand sequence.

In the artificial match-type miRNA of the present invention, when the aforementioned X region and the aforementioned Y region are aligned, the aforementioned Y region has a sequence completely complementary to the aforementioned X region. The aforementioned Y region may consist only of, for example, a sequence completely complementary to the aforementioned X region, or further have an overhang in addition to the aforementioned complementary sequence. That is, in the artificial match-type miRNA of the present invention, when, for example, the aforementioned Y region and the aforementioned X region are aligned, the aforementioned Y region may have an overhang on the 3'-terminal. As use herein, the aforementioned overhang in the Y region is, for example, a terminal base that the aforementioned Y region has in excess than the aforementioned X region when the aforementioned Y region and the aforementioned X region are aligned. The length (O) of the overhang is, for example, as shown in the following formula.

length (O) of overhang=[full-length base number (Y) of Y region]−[full-length base number (X) of X region]

In the artificial match-type miRNA of the present invention, the length of each region is not particularly limited. While examples of the conditions are shown below, the artificial match-type miRNA of the present invention is not limited by such description. In the present invention, the numerical range of the base number discloses all positive integers that fall within the range and, for example, "1-4 bases" means all of "1, 2, 3, 4 bases" (hereinafter the same).

In the aforementioned X region, the length of the aforementioned guide strand sequence is not particularly limited and may be, for example, the length of a guide strand sequence of a reported mature miRNA. Specific examples thereof include a lower limit of 19 base length, 20 base length, and an upper limit of 25 base length, 24 base length, and ranges of 19-25 base length, 20-24 base length.

The length of the aforementioned additional sequence of the aforementioned X region is not particularly limited, and the lower limit is, for example, 0 base length, 1 base length, 2 base length, and the upper limit is, for example, 5 base length, 4 base length, 3 base length, and the range is, for example, 0-5 base length, 1-5 base length, 1-4 base length, 2-3 base length, 3-5 base length.

The length of the aforementioned X region is not particularly limited, the lower limit is, for example, 19 base length, 21 base length, 23 base length, the upper limit is, for example, 30 base length, 28 base length, 26 base length, and the range is, for example, 19-30 base length, 21-28 base length, 23-26 base length.

The length of the aforementioned overhang in the aforementioned Y region is not particularly limited, and the lower limit is, for example, 0 base length, 1 base length, and the upper limit is, for example, 4 base length, 3 base length, and the range is, for example, 0-4 base length, 1-3 base length, 2 base length.

The sequence of the aforementioned overhang is not particularly limited and is, for example, UU, CU, GC, UA, AA, CC, UG, CG, AU, TT and the like from the 3'-side. The aforementioned overhang can be imparted with resistance to ribonuclease by being, for example, TT.

The length of the aforementioned Y region is not particularly limited, and the lower limit is, for example, 19 base length, 21 base length, 23 base length, and the upper limit is, for example, 32 base length, 30 base length, 28 base length, and the range is, for example, 19-32 base length, 21-30 base length, 23-28 base length.

The full-length (T) of the artificial match-type miRNA of the present invention is not particularly limited, and the lower limit is, for example, 38 base length, 42 base length, 46 base length, the upper limit is, for example, 62 base length, 58 base length, 54 base length, and the range is, for example, 38-62 base length, 42-58 base length, 46-54 base length.

In the artificial match-type miRNA of the present invention, the kind of the aforementioned mature miRNA is not particularly limited, and can be appropriately selected according to the kind of the target gene.

Examples of the aforementioned mature miRNA include mature miRNAs such as hsa-miR-34a (SEQ ID NO: 1), hsa-let-7a (SEQ ID NO: 2), hsa-let-7f (SEQ ID NO: 3), hsa-miR-150 (SEQ ID NO: 4), hsa-miR-29b (SEQ ID NO: 5) and the like.

hsa-miR-34a
(SEQ ID NO: 1)
UGGCAGUGUCUUAGCUGGUUGU hsa-let-7a
(SEQ ID NO: 2)
UGAGGUAGUAGGUUGUAUAGUU hsa-let-7f
(SEQ ID NO: 3)
UGAGGUAGUAGGUUGUAUAGUU hsa-miR-150
(SEQ ID NO: 4)
UCUCCCAACCCUUGUACCAGUG hsa-miR-29b
(SEQ ID NO: 5)
UAGCACCAUUUGAAAUCAGUGUU The nucleotide sequence shown in each SEQ ID NO is a guide strand sequence.

The guide strand of miR-34a targets, for example, AXL, MET, CDK4, CDK6, SIRT1, CCND1, SIRT1, BCL-2 and the like, and the suppression of the expression of these target genes can prevent or treat diseases such as lung cancer, colorectal cancer, stomach cancer, liver cancer, breast cancer and the like.

The guide strand of let-7a targets, for example, HMGA2 (high mobility group AT-hook 2), KRAS, NRAS, HRAS, MYC, TLR4 and the like, and the suppression of the expression of these target genes can prevent or treat diseases such as lung cancer, colorectal cancer, stomach cancer, liver cancer, breast cancer and the like.

The guide strand of let-7f targets, for example, HMGA2 (high mobility group AT-hook 2), KRAS, NRAS, HRAS, MYC, TLR4 and the like, and the suppression of the expression of these target genes can prevent or treat diseases such as lung cancer, colorectal cancer, stomach cancer, liver cancer, breast cancer and the like.

The guide strand of miR-150 targets, for example, COL1A1, COL4A4, SMAD2, SP1 and the like, and the suppression of the expression of these target genes can prevent or treat diseases such as lung fibrosis, hepatic fibrosis and the like.

The guide strand of miR-29b targets, for example, COL1A1, MCL1, DNMT3A, DNMT3B, TCL1A, TGFb3 and the like, and the suppression of the expression of these target genes can prevent or treat diseases such as lung cancer, colorectal cancer, stomach cancer, liver cancer, breast cancer, lung fibrosis, hepatic fibrosis and the like.

The constitution units of the artificial match-type miRNA of the present invention are not particularly limited. Examples thereof include nucleotide residues. Examples of the aforementioned nucleotide residues include a ribonucleotide residue and a deoxyribonucleotide residue. In the artificial match-type miRNA of the present invention, the aforementioned nucleotide residue is preferably, for example, a ribonucleotide residue. The aforementioned nucleotide residue may be, for example, the one that is not modified (unmodified nucleotide residue) or the one that has been modified (modified nucleotide residue). By configuring the artificial match-type miRNA of the present invention to include the aforementioned modified nucleotide residue, for example, the resistance of the artificial match-type miRNA to nuclease can be improved, thereby allowing the stability of the artificial match-type miRNA to be improved. Furthermore, the artificial match-type miRNA of the present invention further may include, for example, a non-nucleotide residue in addition to the aforementioned nucleotide residue.

When the artificial match-type miRNA includes, for example, the aforementioned modified ribonucleotide residue(s) in addition to the aforementioned unmodified ribonucleotide residues, the number of the aforementioned modified ribonucleotide residue(s) is not particularly limited, and is, for example, "one to several", specifically, for example, 1 to 5, preferably 1 to 4, more preferably 1 to 3, and most preferably 1 or 2. The aforementioned modified ribonucleotide residue as contrasted to the aforementioned unmodified ribonucleotide residue may be, for example, the aforementioned deoxyribonucleotide residue obtained by substituting a ribose residue with a deoxyribose residue. When the artificial match-type miRNA of the present invention includes, for example, the aforementioned deoxyribonucleotide residue(s) in addition to the aforementioned unmodified ribonucleotide residue(s), the number of the aforementioned deoxyribonucleotide residue(s) is not particularly limited, and is, for example, "one to several", specifically, for example, 1 to 5, preferably 1 to 4, more preferably 1 to 3, and most preferably 1 or 2.

The aforementioned nucleotide residue includes, for example, a sugar, a base, and a phosphate as its components. The aforementioned ribonucleotide residue has, for example, a ribose residue as the sugar; and adenine (A), guanine (G), cytosine (C), or uracil (U) as the base. The aforementioned deoxyribose residue has, for example, a deoxyribose residue as the sugar; and adenine (A), guanine (G), cytosine (C), or thymine (T) as the base.

The aforementioned components of the aforementioned unmodified nucleotide residue are the same or substantially the same as, for example, the components of a naturally-occurring nucleotide residue. Specifically, for example, the components are the same or substantially the same as the components of a nucleotide residue occurring naturally in a human body.

For example, the aforementioned modified nucleotide residue may be such that any of the components of the aforementioned unmodified nucleotide residue is modified. Examples of the aforementioned modified nucleotide residue include naturally-occurring nucleotide residues and artificially-modified nucleotide residues.

The aforementioned modified nucleotide residue may be, for example, a residue of an alternative of the aforementioned nucleotide. Examples of the aforementioned alternative include artificial nucleic acid monomer residues. Specific examples thereof include PNA (Peptide Nucleic Acid), LNA (Locked Nucleic Acid), and ENA (2'—O,4'-C-Ethylenebridged Nucleic Acids).

In the aforementioned nucleotide residue, the aforementioned base is not particularly limited. The aforementioned base may be, for example, a natural base or a non-natural base. The aforementioned base may be, for example, a naturally-derived base or a synthetic base. As the aforementioned base, for example, a common base, a modified analog thereof, and the like can be used.

In the artificial match-type miRNA of the present invention, the linker region of the aforementioned non-nucleotide structure preferably contains at least one selected from the group consisting of an amino acid residue, a polyamine residue and a polycarboxylic acid residue. The aforementioned linker region may or may not contain a residue other than the amino acid residue, polyamine residue and polycarboxylic acid residue. For example, the aforementioned linker region may contain any of a polycarboxylic acid residue, a terephthalic acid residue and an amino acid residue.

In the present invention, the "polyamine" means any compound containing a plurality of (two, three or more) amino groups. The aforementioned "amino group" is not limited to an —NH$_2$ group and also includes an imino group (—NH—). In the present invention, the aforementioned polyamine is not particularly limited, and examples thereof include 1,4-diaminobenzene, 1,3-diaminobenzene, 1,2-diaminobenzene and the like. In the present invention, moreover, the "polycarboxylic acid" means any compound containing a plurality of (two, three or more) carboxy groups. In the present invention, the aforementioned polycarboxylic acid is not particularly limited, and examples thereof include 1,4-dicarboxybenzene (terephthalic acid), 1,3-dicarboxybenzene (isophthalic acid), 1,2-dicarboxybenzene (phthalic acid) and the like. In the present invention, moreover, the "amino acid" means any organic compound containing one or more amino groups and one or more carboxy groups in a molecule, as mentioned below. The aforementioned "amino group" is not limited to an —NH$_2$ group and also includes an imino group (—NH—).

In the artificial match-type miRNA of the present invention, the aforementioned amino acid residue may be composed of a plurality of interlinked amino acid residues. In the present invention, the amino acid residue that is a plurality of interlinked amino acid residues is, for example, a residue containing a peptide structure. More specifically, the aforementioned amino acid residue that is a plurality of interlinked amino acid residues is, for example, an amino acid residue of the below-mentioned chemical formula (I) wherein the below-mentioned chemical formula (Ia) is a peptide (e.g., glycine dimer or glycine trimer etc.).

In the artificial match-type miRNA of the present invention, the aforementioned amino acid residue may be a glycine residue, a terephthalic acid amide residue, a proline residue or a lysin residue. The aforementioned amino acid residue may be a modified amino acid residue or an amino acid derivative.

In the artificial match-type miRNA of the present invention, the aforementioned linker region is represented by, for example, the following chemical formula (I-0).

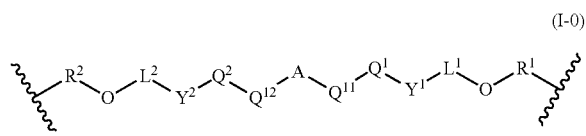

(I-0)

in the aforementioned chemical formula (I-0),
Q11 and Q12 are each independently a single bond, CH$_2$ (a methylene group), NH (an imino group), C=O (a carbonyl group),
C=S (a thiocarbonyl group), C=NH (an iminomethylene group), O, or S,
Q1 and Q2 are each independently a single bond, CH$_2$ (a methylene group), NH (an imino group), C=O (a carbonyl group), C=S (a thiocarbonyl group), C=NH (an iminomethylene group), O, or S,
$Y^1$ and $Y^2$ are each independently a single bond, CH$_2$, NH, O, or S;

$L^1$ is an alkylene chain having n carbon atoms, and a hydrogen atom on an alkylene carbon atom may or may not be substituted with OH, $OR^a$, $NH_2$, $NHR^a$, $NR^aR^b$, SH, or $SR^a$, or, L1 is a polyether chain obtained by substituting at least one carbon atom on the aforementioned alkylene chain with an oxygen atom, provided that: when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or $L^2$ is a polyether chain obtained by substituting at least one carbon atom on the aforementioned alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30;

the aforementioned regions X and Y are each linked to the aforementioned linker residue via $-OR^1-$ or $-OR^2-$, wherein $R^1$ and $R^2$ may or may not be present, and when they are present, $R^1$ and $R^2$ are each independently a nucleotide residue or the aforementioned structure (I-0); and A is any atomic group.

The combination of the aforementioned regions (X) and (Y) with $-OR^1-$ and $-OR^2-$ is not particularly limited, and may be, for example, any of the following conditions.

Condition (1):
the aforementioned regions (X) and (Y) are linked to the structure of the aforementioned formula (I) via $-OR^2-$ and $-OR^1-$, respectively.

Condition (2):
the aforementioned regions (X) and (Y) are linked to the structure of the aforementioned formula (I) via $-OR^1-$ and $-OR^2-$, respectively.

In the aforementioned chemical formula (I-0), for example, $Q^{11}$ may be C=O (a carbonyl group), and $Q^1$ may be NH (an imino group). In addition, for example, $Q^{11}$ may may be NH (an imino group), and $Q^1$ may be C=O (a carbonyl group).

Furthermore, for example, $Q^{12}$ may be C=O (a carbonyl group), and $Q^2$ may be NH (an imino group). Moreover, for example, $Q^{12}$ may be NH (an imino group), and $Q^2$ may be C=O (a carbonyl group).

In the aforementioned chemical formula (I-0), each of $Q^{11}$ and $Q^{12}$ may be, for example, a carbonyl group. In this case, each of $Q^1$ and $Q^2$ is preferably an imino group. In addition, in this case, the structure of the following chemical formula (Iα) is more preferably represented by the following chemical formula (Iα2).

(Iα)

(Iα2)

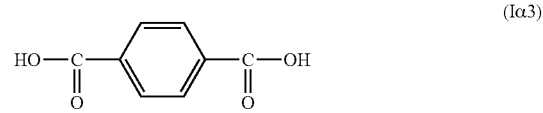

In the aforementioned chemical formula (Iα2), $R^{100}$ is a any substituent, which may or may not be present. When it is present, it may be present singly or in plurality. When it is present in plurality, they may be the same or different from each other. Examples of the aforementioned any substituent for $R^{100}$ include the below-mentioned substituents exemplified as the aforementioned $R^a$, $R^b$, $R^c$ and $R^d$. More specific examples thereof include halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl and the like. The structure of the aforementioned chemical formula (Iα12) is more preferably represented by the following chemical formula (Iα3).

(Iα3)

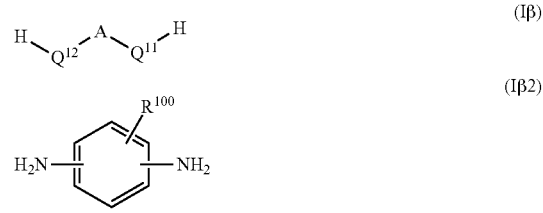

When $Q^{11}$ and $Q^{12}$ are carbonyl groups, and $Q^1$ and $Q^2$ are imino groups, the linker residue of the aforementioned chemical formula (I-0) can be a carboxylic acid amide residue or a carboxylic acid residue. For example, the "TPA" structure in the below-mentioned Example can be a terephthalamide residue or a terephthalic acid residue represented by the aforementioned chemical formula (Iα3).

In the aforementioned chemical formula (I-0), each of $Q^{11}$ and $Q^{12}$ may be an imino group. In this case, each of $Q^1$ and $Q^2$ is preferably a carbonyl group. In this case, the structure of the following chemical formula (Iβ) is more preferably represented by the following chemical formula (Iβ2).

(Iβ)

(Iβ2)

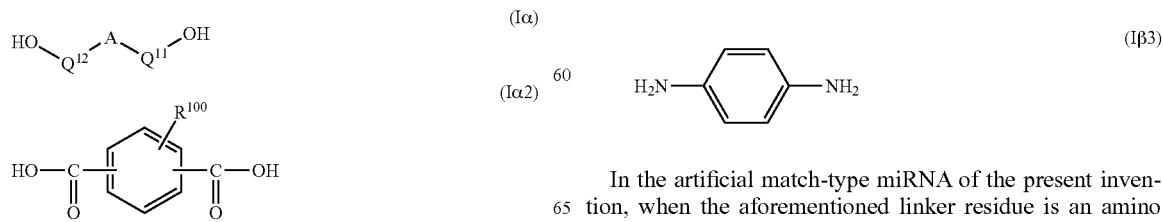

In the aforementioned chemical formula (Iβ2), $R^{100}$ is any substituent, which may or may not be present. When it is present, it may be present singly or in plurality. When it is present in plurality, they may be the same or different from each other. Specifically, for example, it is the same as $R^{100}$ in the aforementioned chemical formula (Iα2). In addition, the structure of the aforementioned chemical formula (Iβ2) is more preferably represented by the following chemical formula (Iβ3).

(Iβ3)

In the artificial match-type miRNA of the present invention, when the aforementioned linker residue is an amino acid residue, the aforementioned amino acid residue is represented by, for example, the following chemical formula (I). The structure of the following chemical formula (I) is one example of the structure represented by the aforementioned chemical formula (I-0).

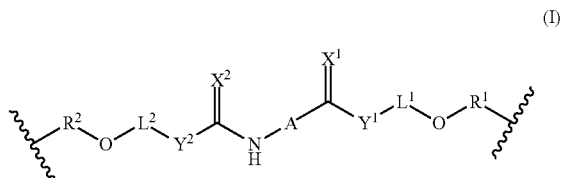

(I)

In the aforementioned formula (I), for example, $X^1$, $X^2$, $Y^1$, $Y^2$, $L^1$ and $L^2$ are as defined above.

The sequence complementary to the sequence of the aforementioned microRNA is each bound to the aforementioned amino acid residue via —$OR^1$— or —$OR^2$—,
wherein $R^1$ and $R^2$ may or may not be present, and when they are present, $R^1$ and $R^2$ are each independently a nucleotide residue or the aforementioned structure (I); and
A is any atomic group, provided that the following chemical formula (Ia) is an amino acid or peptide.

(Ia)

The atomic group A in the aforementioned chemical formula (I), (Iα) or (Ia) may or may not contain, for example, at least one selected from the group consisting of chain atomic group, alicyclic atomic group, aromatic atomic group, heteroaromatic atomic group, and heteroalicyclic atomic group. While the aforementioned chain atomic group is not particularly limited, for example, alkyl, alkenyl, alkynyl, haloalkyl, hydroxyalkyl, alkoxyalkyl, aminoalkyl, silyl, silyloxyalkyl and the like can be mentioned. While the aforementioned alicyclic atomic group is not particularly limited, for example, cycloalkyl, cycloalkenyl, cycloalkylalkyl, cyclylalkyl and the like can be mentioned. While the aforementioned aromatic atomic group is not particularly limited, for example, aryl, arylalkyl, alkylaryl, condensed-ring aryl, condensed-ring arylalkyl, condensed-ring alkylaryl and the like can be mentioned. The aforementioned heteroaromatic atomic group is not particularly limited, and examples thereof include heteroaryl, heteroarylalkyl, alkylheteroaryl, condensed-ring heteroaryl, condensed-ring heteroarylalkyl, condensed-ring alkylheteroaryl and the like. In the atomic group A in the aforementioned chemical formula (I), (Iα) or (Ia), each of the aforementioned atomic groups may or may not further have a substituent or a protecting group. When the aforementioned substituent or protecting group is in plurality, they may be the same or different. The aforementioned substituents are, for example, those exemplified for the aforementioned $R^a$, $R^b$, $R^c$ and $R^d$, more specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. The aforementioned protecting groups are, for example, the same as those exemplified for the aforementioned $R^a$, $R^b$, $R^c$ and $R^d$.

In the present invention, the "amino acid" refers to, as mentioned above, any organic compound containing at least one amino group and at least one carboxy group in a molecule. The aforementioned "amino group" is not limited to —$NH_2$ group, and also includes imino group (—NH—). For example, proline, hydroxyproline and the like not containing —$NH_2$ group in a molecule but containing imino group (—NH—) is included in the definition of the "amino acid" in the present invention. In the present invention, the aforementioned "amino acid" may be, as mentioned below, a natural amino acid or an artificial amino acid. For example, since a compound represented by the below-mentioned chemical formula (Ia2) or (Ia3) contains an amino group and a carboxy group in a molecule, it is encompassed in the definition of the "amino acid" in the present invention. Therefore, for example, the aforementioned chemical formula (I) wherein the atomic group A is a structure shown by the below-mentioned chemical formula (A2) or chemical formula (A2a) is included in the definition of "amino acid residue" in the present invention. For example, the "TPA" structure in the below-mentioned Example is also included in the definition of the "amino acid residue" in the present invention. The "peptide" in the present invention refers to an organic compound having a structure wherein not less than 2 molecules of amino acid are bonded via a peptide bond. The aforementioned peptide bond may be an acid amide structure or an acid imide structure. When plural amino groups are present in the amino acid or peptide molecule represented by the aforementioned chemical formula (Ia), the amino group clearly shown in the aforementioned chemical formula (Ia) may be any amino group. In addition, when plural carboxy groups are present in the amino acid or peptide molecule represented by the aforementioned chemical formula (Ia), the carboxy group clearly shown in the aforementioned chemical formula (Ia) may be any carboxy group.

In the aforementioned amino acid residue of the artificial match-type miRNA of the present invention, the aforementioned amino acid may be, as mentioned above, natural amino acid or artificial amino acid. In the present invention, the "natural amino acid" refers to an amino acid having a naturally-occurring structure or an optical isomer thereof. The production method of the aforementioned natural amino acid is not particularly limited and, for example, it may be extracted from the nature, or may be synthesized. In the present invention, moreover, the "artificial amino acid" refers to an amino acid having a structure not occurring naturally. That is, the aforementioned artificial amino acid is an amino acid, i.e., a carboxylic acid derivative containing an amino group (organic compound containing at least one amino group and at least one carboxy group in a molecule) and having a structure not occurring naturally. The aforementioned artificial amino acid preferably does not contain, for example, a hetero ring. The aforementioned amino acid may be an amino acid constituting, for example, a protein. The aforementioned amino acid may be, for example, at least one kind selected from the group consisting of glycine, α-alanine, arginine, asparagine, aspartic acid, cysteine, cystine, glutamine, glutamic acid, histidine, isoleucine, leucine, lysine, hydroxylysine, methionine, phenylalanine, serine, threonine, tyrosine, valine, proline, 4-hydroxyproline, tryptophan, β-alanine, 1-amino-2-carboxycyclopentane, aminobenzoic acid, aminopyridinecarboxylic acid and amino acid represented by the following chemical formula (Ia2), and may or may not further have a substituent or a protecting group. Examples of the aforementioned substituent include the substituents exemplified for the aforementioned Ra, Rb, Rc and Rd. More specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like can be mentioned. The aforementioned protecting group is the same as, for example, the protecting groups exemplified for the aforementioned Ra, Rb, Rc and Rd. When the amino acid of the aforementioned chemical formula (Ia), which is not peptide, contains isomers such as optical isomer, geometric isomer, stereoisomer and the like, any isomer can be used.

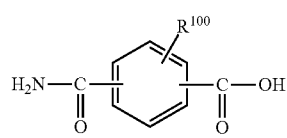

(Ia2)

In the aforementioned chemical formula (Ia2), R100 is an optional substituent and may or may not be present. When it is present, the number thereof may be one or more and, when it is present in plurality, they may be the same or different. Examples of the aforementioned optional substituent for R100 include the substituents exemplified for the aforementioned Ra, Rb, Rc and Rd, more specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. The structure of the aforementioned chemical formula (Ia2) may be, for example, the following chemical formula (Ia3).

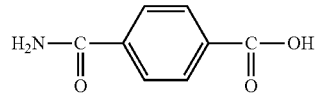

(Ia3)

When the structure of the aforementioned chemical formula (Ia) is the aforementioned chemical formula (Ia2), the structure of the atomic group A in the aforementioned chemical formula (I) is represented by the following chemical formula (A2). R100 in the following chemical formula (A2) is the same as that in the aforementioned chemical formula (Ia2). When the structure of the aforementioned chemical formula (Ia) is the aforementioned chemical formula (Ia3), the structure of the atomic group A in the aforementioned chemical formula (I) is represented by the following chemical formula (A2a).

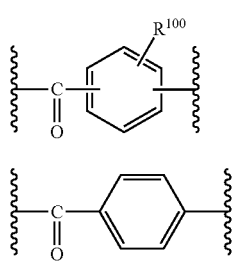

The structure of the aforementioned chemical formula (I) is, for example, the following chemical formulae (I-1)-(I-7), wherein n and m are the same as those in the aforementioned chemical formula (I).

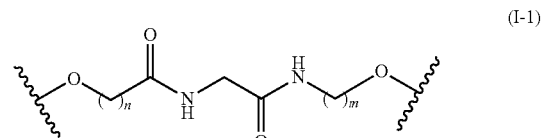

(I-1)

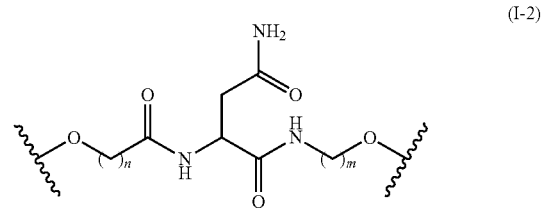

(I-2)

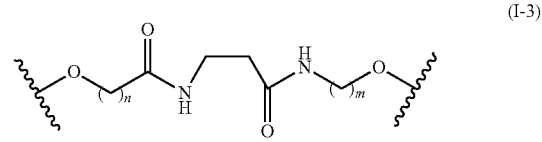

(I-3)

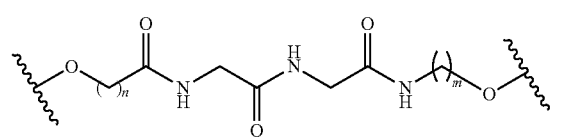

(I-4)

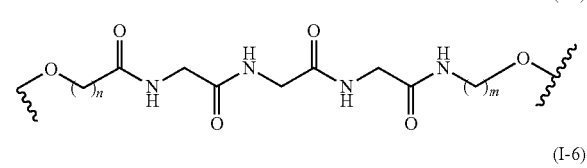

(I-5)

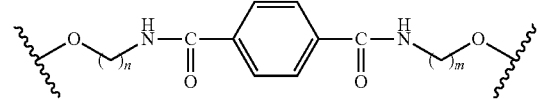

(I-6)

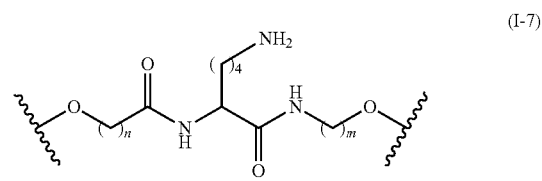

(I-7)

In the aforementioned chemical formulae (I-1)-(I-7), n and m are not particularly limited, and as described above. Specific examples thereof include n=11 and m=12 or n=5 and m=4 in the aforementioned chemical formula (I-1), n=5 and m=4 in the aforementioned chemical formula (I-4), n=4 and m=4 in the aforementioned chemical formula (I-6), and n=5 and m=4 in the aforementioned chemical formula (1-7). The structures thereof are shown in the following chemical formulae (I-1a), (I-1b) (I-4a), (I-6a) and (I-7a).

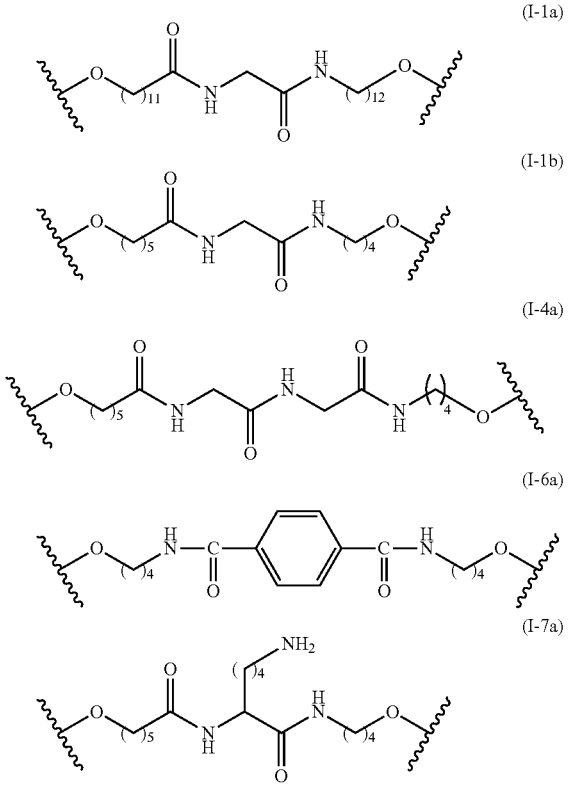

In the artificial match-type miRNA of the present invention, the aforementioned linker region is represented, for example, by the following formula (II):

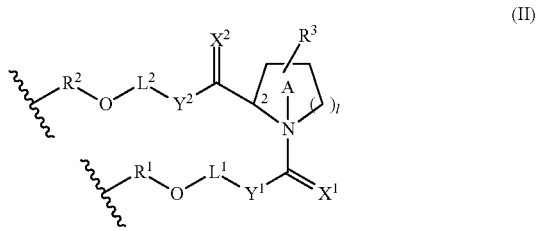

In the aforementioned formula (II), for example, $X^1$ and $X^2$ are each independently $H_2$, O, S, or NH;

$Y^1$ and $Y^2$ are each independently a single bond, $CH_2$, NH, O, or S;

$R^3$ is a hydrogen atom or a substituent which is bonded to C-3, C-4, C-5 or C-6 on ring A, $L^1$ is an alkylene chain having n atoms, and a hydrogen atom on an alkylene carbon atom may or may not be substituted with OH, $OR^a$, $NH_2$, $NHR^a$, $NR^aR^b$, SH, or $SR^a$, or, $L^1$ is a polyether chain obtained by substituting at least one carbon atom on the aforementioned alkylene chain with an oxygen atom, provided that: when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain having m atoms, and a hydrogen atom on an alkylene carbon atom may or may not be substituted with OH, $OR^c$, $NH_2$, $NHR^c$, $NR^cR^d$, SH, or $SR^c$, or $L^2$ is a polyether chain obtained by substituting at least one carbon atom on the aforementioned alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

l is 1 or 2;

m is an integer in the range from 0 to 30;

n is an integer in the range from 0 to 30; and in ring A, one carbon atom other than the aforementioned C-2 on the ring A may be substituted by nitrogen, oxygen or sulfur, and may contain, in the aforementioned ring A, a carbon-carbon double bond or a carbon-nitrogen double bond, the aforementioned regions (X) and (Y) are each linked to the aforementioned non-nucleotide structure via —$OR^1$— or —$OR^2$—, wherein $R^1$ and $R^2$ may or may not be present, and when they are present, $R^1$ and $R^2$ are each independently a nucleotide residue or the aforementioned structure (II).

In the aforementioned formula (II), for example, $X^1$ and $X^2$ are each independently $H_2$, O, S, or NH. In the aforementioned formula (II), "$X^1$ is $H_2$" means that $X^1$ forms $CH_2$ (a methylene group) together with a carbon atom to which $X^1$ binds. The same applies to $X^2$.

In the aforementioned formula (II), $Y^1$ and $Y^2$ are each independently a single bond, $CH_2$, NH, O, or S.

In the aforementioned formula (II), l in ring A is 1 or 2. When l=1, ring A is a 5-membered ring, for example, the aforementioned pyrrolidine skeleton. The aforementioned pyrrolidine skeleton is, for example, proline skeleton, prolinol skeleton or the like, and exemplified by the divalent structures thereof. When l=2, ring A is a 6-membered ring, for example, the aforementioned piperidine skeleton. In ring A, one carbon atom other than C-2 on ring A may be substituted by nitrogen, oxygen or sulfur. Ring A may contain, in ring A, a carbon-carbon double bond or a carbon-nitrogen double bond. Ring A is, for example, L type or D type.

In the aforementioned formula (II), $R^3$ is a hydrogen atom or substituent bonded to C-3, C-4, C-5 or C-6 on ring A. When $R^3$ is the aforementioned substituent, substituent $R^3$ may be one or more, or may be absent. When $R^3$ is present in plurality, they may be the same or different.

The substituent $R^3$ is, for example, halogen, OH, $OR^4$, $NH_2$, $NHR^4$, $NR^4R^5$, SH, $SR^4$, oxo group (=O) and the like.

$R^4$ and $R^5$ are, for example, each independently a substituent or a protecting group, and may be the same or different. Examples of the aforementioned substituent include halogen, alkyl, alkenyl, alkynyl, haloalkyl, aryl, heteroaryl, arylalkyl, cycloalkyl, cycloalkenyl, cycloalkylalkyl, cyclylalkyl, hydroxyalkyl, alkoxyalkyl, aminoalkyl, heterocyclylalkenyl, heterocyclylalkyl, heteroarylalkyl, silyl, silyloxyalkyl and the like. The same applies hereinafter. The substituent $R^3$ may be selected from the substituents recited above.

The aforementioned protecting group is a functional group that inactivates, for example, a highly-reactive functional group. Examples of the protecting group include known protecting groups and the like. Regarding the aforementioned protecting group, for example, the description in the literature (J. F. W. McOmie, "Protecting Groups in Organic Chemistry", Prenum Press, London and New York, 1973) can be incorporated herein. The aforementioned protecting group is not particularly limited, and examples thereof include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM), a tolylsulfonylethoxymethyl group (TEM), a dimethoxytrityl group (DMTr) and the like. When $R^3$ is $OR^4$, the aforementioned protecting group is not particularly limited, and examples thereof include a TBDMS group, an ACE group, a TOM group, a CEE group, a CEM group, a TEM group and the like. Other examples of the protecting group include silyl-containing groups. The same applies hereinafter.

In the aforementioned formula (II), $L^1$ is an alkylene chain having n atoms. A hydrogen atom(s) on the aforementioned alkylene carbon atom(s) may or may not be substituted with, for example, OH, $OR^a$, $NH_2$, $NHR^a$, $NR^aR^b$, SH, or $SR^a$. Alternatively, $L^1$ may be a polyether chain obtained by substituting at least one carbon atom on the aforementioned alkylene chain with an oxygen atom. The aforementioned polyether chain is, for example, polyethylene glycol. When $Y^1$ is NH, O, or S, an atom bound to $Y^1$ in $L^1$ is carbon, an atom bound to $OR^1$ in $L^1$ is carbon, and oxygen atoms are not adjacent to each other. That is, for example, when $Y^1$ is O, this oxygen atom and the oxygen atom in $L^1$ are not adjacent to each other, and the oxygen atom in $OR^1$ and the oxygen atom in $L^1$ are not adjacent to each other.

In the aforementioned formula (II), $L^2$ is an alkylene chain having m atoms. A hydrogen atom(s) on the aforementioned alkylene carbon atom(s) may or may not be substituted with, for example, OH, $OR^c$, $NH_2$, $NHR^c$, $NR^cRd$, SH, or $SR^c$. Alternatively, $L^2$ may be a polyether chain obtained by substituting at least one carbon atom on the aforementioned alkylene chain with an oxygen atom. When $Y^2$ is NH, O, or S, an atom bound to $Y^2$ in $L^2$ is carbon, an atom bound to $OR^2$ in $L^2$ is carbon, and oxygen atoms are not adjacent to each other. That is, for example, when $Y^2$ is O, this oxygen atom and the oxygen atom in $L^2$ are not adjacent to each other, and the oxygen atom in $OR^2$ and the oxygen atom in $L^2$ are not adjacent to each other.

n of $L^1$ and m of $L^2$ are not particularly limited, and the lower limit of each of them may be 0, for example, and the upper limit of the same is not particularly limited. For example, n and m can be set as appropriate depending on a desired length of the aforementioned non-nucleotide structure. For example, from the view point of manufacturing cost, yield, and the like, n and m are each preferably 0 to 30, more preferably 0 to 20, and still more preferably 0 to 15. n and m may be the same (n=m) or different. n+m is, for example, 0 to 30, preferably 0 to 20, and more preferably 0 to 15.

For example, $R^a$, $R^b$, $R^c$ and $R^d$ are each independently a substituent or a protecting group. Examples of the aforementioned substituent and the aforementioned protecting group are the same as above.

In the aforementioned formula (II), hydrogen atoms each independently may be substituted with, for example, a halogen such as Cl, Br, F, I and the like.

The aforementioned X region and the aforementioned Y region are each bound to the aforementioned non-nucleotide structure via, for example, —$OR^1$— or —$OR^2$—. Here, $R^1$ and $R^2$ may or may not be present. When $R^1$ and $R^2$ are present, $R^1$ and $R^2$ are each independently a nucleotide residue or the structure represented by the aforementioned formula (II). When $R^1$ and/or $R^2$ are/is the aforementioned nucleotide residue, the aforementioned non-nucleotide structure is formed by, for example, the aforementioned non-nucleotide residue having the structure of the aforementioned formula (II) excluding the nucleotide residue $R^1$ and/or $R^2$, and the aforementioned nucleotide residue(s). When $R^1$ and/or $R^2$ are/is the structure represented by the aforementioned formula (II), the structure of the aforementioned non-nucleotide structure is such that, for example, two or more of the aforementioned non-nucleotide residues having the structure of the aforementioned formula (II) are linked to each other. The number of the structures of the aforementioned formula (II) may be, for example, 1, 2, 3, or 4. When the aforementioned structure includes a plurality of the aforementioned structures, the structures of the aforementioned (II) may be linked, for example, either directly or via the aforementioned nucleotide residue(s). On the other hand, when $R^1$ and $R^2$ are not present, the aforementioned non-nucleotide structure is formed by, for example, the aforementioned non-nucleotide residue having the structure of the aforementioned formula (II) alone.

The combination of the aforementioned regions X and Y with —$OR^1$— and —$OR^2$— is not particularly limited, and may be, for example, any of the following conditions:

conditions (1)

the aforementioned regions X and Y are linked to the structure of the aforementioned formula (II) via —$OR^2$— and —$OR^1$—, respectively;

conditions (2)

the aforementioned regions X and Y are linked to the structure of the aforementioned formula (II) via —$OR^1$— and —$OR^2$—, respectively;

Examples of the structure of the aforementioned formula (II) include the structures of the following formulae (II-1) to (II-9). In the following formulae, n and m are the same as in the aforementioned formula (II). In the following formulae, q is an integer of 0-10.

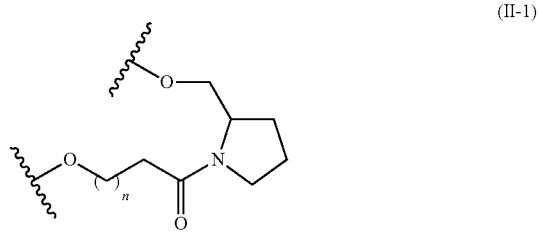

(II-1)

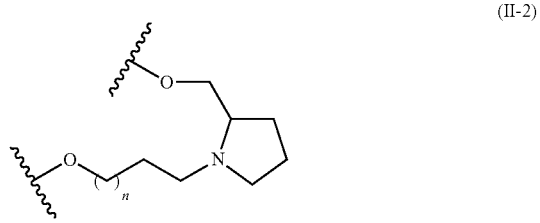

(II-2)

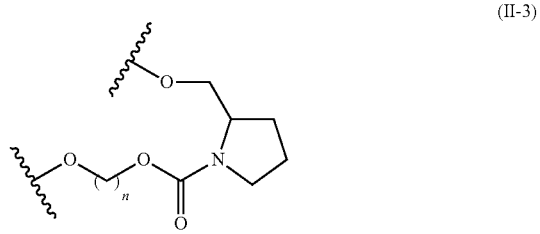

(II-3)

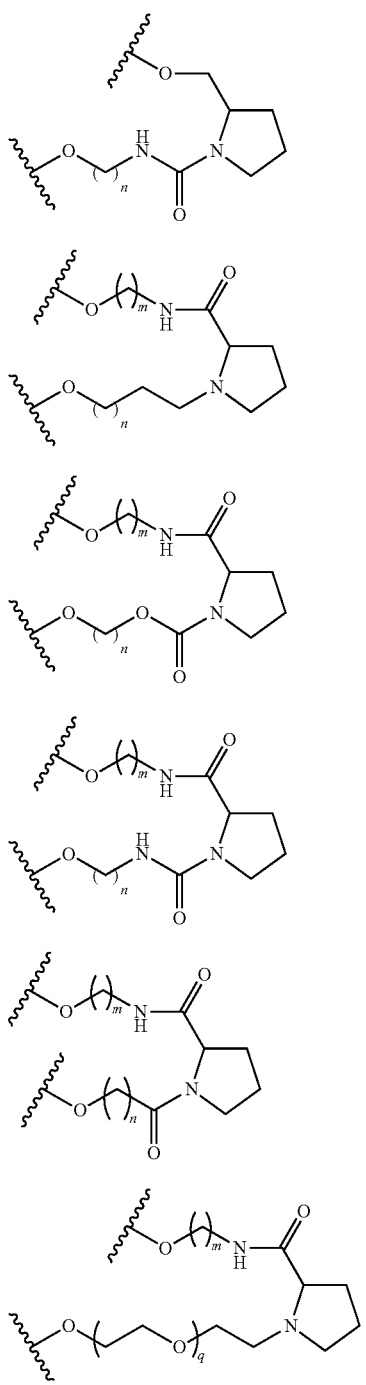

(II-4)

(II-5)

(II-6)

(II-7)

(II-8)

(II-9)

In the aforementioned formulae (II-1) to (II-9), n, m and q are not particularly limited, and are as described above. Specific example thereof is the aforementioned formula (II-1) wherein n=8, the aforementioned (II-2) wherein n=3, the aforementioned formula (II-3) wherein n=4 or 8, the aforementioned (II-4) wherein n=7 or 8, the aforementioned formula (II-5) wherein n=3 and m=4, the aforementioned (II-6) wherein n=8 and m=4, the aforementioned formula (II-7) wherein n=8 and m=4, the aforementioned formula (II-8) wherein n=5 and m=4, and the aforementioned formula (II-9) wherein q=1 and m=4. One embodiment (n=8) of the aforementioned formula (II-4) is shown in the following formula (II-4a), and one embodiment(n=5, m=4) of the aforementioned formula (II-8) is shown in the following formula (II-8a).

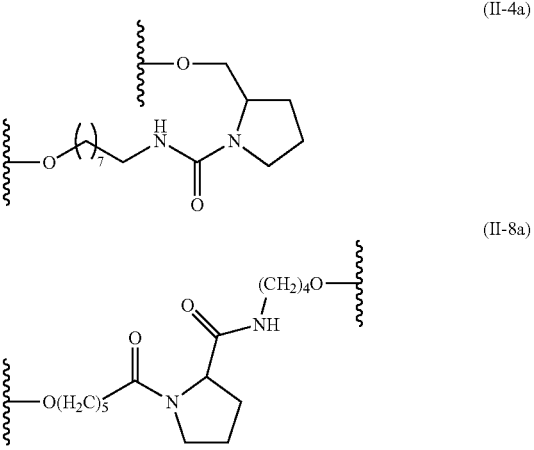

In the present invention, the term "alkyl" encompasses, for example, straight-chain and branched alkyl groups. The number of carbon atoms in the aforementioned alkyl is not particularly limited, and is, for example, 1 to 30, preferably 1 to 6, more preferably 1 to 4. Examples of the aforementioned alkyl group include: methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, and n-decyl and the like. Among them, for example, methyl, ethyl, n-propyl, isopropyl, n-butyl, isobutyl, sec-butyl, tert-butyl, n-pentyl, isopentyl, neopentyl, n-hexyl, isohexyl, and the like are preferable.

In the present invention, the term "alkenyl" encompasses, for example, straight-chain and branched alkenyls. Examples of the aforementioned alkenyl include the aforementioned alkyls having one or more double bonds and the like. The number of carbon atoms in the aforementioned alkenyl is not particularly limited, and is, for example, the same as that in the aforementioned alkyl, preferably 2 to 8. Examples of the aforementioned alkenyl include vinyl, 1-propenyl, 2-propenyl, 1-butenyl, 2-butenyl, 3-butenyl, 1,3-butadienyl, 3-methyl-2-butenyl and the like.

In the present invention, the term "alkynyl" encompasses, for example, straight-chain and branched alkynyls. Examples of the aforementioned alkynyl include the aforementioned alkyls having one or more triple bonds and the like. The number of carbon atoms in the aforementioned alkynyl is not particularly limited, and is, for example, the same as that in the aforementioned alkyl, preferably 2 to 8. Examples of the aforementioned alkynyl include ethynyl, propynyl, butynyl and the like. The aforementioned alkynyl may further include, for example, one or more double bonds.

In the present invention, the term "aryl" encompasses, for example, monocyclic aromatic hydrocarbon groups and polycyclic aromatic hydrocarbon groups. Examples of the aforementioned monocyclic aromatic hydrocarbon group include phenyl and the like. Examples of the aforementioned polycyclic aromatic hydrocarbon group include 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl and the like. Among them, for example, phenyl, naphthyls such as 1-naphthyl and 2-naphthyl, and the like are preferable.

In the present invention, the term "heteroaryl" encompasses, for example, monocyclic aromatic heterocyclic groups and condensed aromatic heterocyclic groups. Examples of the aforementioned heteroaryl include furyls (e.g., 2-furyl, 3-furyl), thienyls (e.g., 2-thienyl, 3-thienyl), pyrrolyls (e.g., 1-pyrrolyl, 2-pyrrolyl, 3-pyrrolyl), imidazolyls (e.g., 1-imidazolyl, 2-imidazolyl, 4-imidazolyl), pyrazolyls (e.g., 1-pyrazolyl, 3-pyrazolyl, 4-pyrazolyl), triazolyls (e.g., 1,2,4-triazol-1-yl, 1,2,4-triazol-3-yl, 1,2,4-triazol-4-yl), tetrazolyls (e.g., 1-tetrazolyl, 2-tetrazolyl, 5-tetrazolyl), oxazolyls (e.g., 2-oxazolyl, 4-oxazolyl, 5-oxazolyl), isoxazolyls (e.g., 3-isoxazolyl, 4-isoxazolyl, 5-isoxazolyl), thiazolyls (e.g., 2-thiazolyl, 4-thiazolyl, 5-thiazolyl), thiadiazolyls, isothiazolyls (e.g., 3-isothiazolyl, 4-isothiazolyl, 5-isothiazolyl), pyridyls (e.g., 2-pyridyl, 3-pyridyl, 4-pyridyl), pyridazinyls (e.g., 3-pyridazinyl, 4-pyridazinyl), pyrimidinyls (e.g., 2-pyrimidinyl, 4-pyrimidinyl, 5-pyrimidinyl), furazanyls (e.g., 3-furazanyl), pyrazinyls (e.g., 2-pyrazinyl), oxadiazolyls (e.g., 1,3,4-oxadiazol-2-yl), benzofuryls (e.g., 2-benzo[b]furyl, 3-benzo[b]furyl, 4-benzo[b]furyl, 5-benzo[b]furyl, 6-benzo[b]furyl, 7-benzo[b]furyl), benzothienyls (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyls (e.g., 1-benzimidazolyl, 2-benzimidazolyl, 4-benzimidazolyl, 5-benzimidazolyl), dibenzofuryls, benzoxazolyls, benzothiazolyls, quinoxalinyls (e.g., 2-quinoxalinyl, 5-quinoxalinyl, 6-quinoxalinyl), cinnolinyls (e.g., 3-cinnolinyl, 4-cinnolinyl, 5-cinnolinyl, 6-cinnolinyl, 7-cinnolinyl, 8-cinnolinyl), quinazolinyls (e.g., 2-quinazolinyl, 4-quinazolinyl, 5-quinazolinyl, 6-quinazolinyl, 7-quinazolinyl, 8-quinazolinyl), quinolyls (e.g., 2-quinolyl, 3-quinolyl, 4-quinolyl, 5-quinolyl, 6-quinolyl, 7-quinolyl, 8-quinolyl), phthalazinyls (e.g., 1-phthalazinyl, 5-phthalazinyl, 6-phthalazinyl), isoquinolyls (e.g., 1-isoquinolyl, 3-isoquinolyl, 4-isoquinolyl, 5-isoquinolyl, 6-isoquinolyl, 7-isoquinolyl, 8-isoquinolyl), puryls, pteridinyls (e.g., 2-pteridinyl, 4-pteridinyl, 6-pteridinyl, 7-pteridinyl), carbazolyls, phenanthridinyls, 5 acridinyls (e.g., 1-acridinyl, 2-acridinyl, 3-acridinyl, 4-acridinyl, 9-acridinyl), indolyls (e.g., 1-indolyl, 2-indolyl, 3-indolyl, 4-indolyl, 5-indolyl, 6-indolyl, 7-indolyl), isoindolyls, phenazinyls (e.g., 1-phenazinyl, 2-phenazinyl), and phenothiazinyls (e.g., 1-phenothiazinyl, 2-phenothiazinyl, 3-phenothiazinyl, 4-phenothiazinyl) and the like.

In the present invention, for example, the term "cycloalkyl" refers to cyclic saturated hydrocarbon groups and the number of carbon atoms in the cycloalkyl is, for example, 3 to 15. Examples of the aforementioned cycloalkyl include cyclopropyl, cyclobutyl, cyclopentyl, cyclohexyl, cycloheptyl, cyclooctyl, bridged cyclic hydrocarbon groups, Spiro hydrocarbon groups and the like. Among them, cyclopropyl, cyclobutyl, cyclopentyl, cyclohexyl, bridged cyclic hydrocarbon groups, and the like are preferable.

In the present invention, examples of the "bridged cyclic hydrocarbon groups" include bicyclo[2.1.0]pentyl, bicyclo[2.2.1]heptyl, bicyclo[2.2.2]octyl, and bicyclo[3.2.1]octyl, tricyclo[2.2.1.0]heptyl, bicyclo[3.3.1]nonane, 1-adamantyl, 2-adamantyl and the like.

In the present invention, examples of the "Spiro hydrocarbon groups" include spiro[3.4]octyl and the like.

In the present invention, the term "cycloalkenyl" encompasses, for example, unsaturated cyclic aliphatic hydrocarbon groups and the number of carbon atoms in the cycloalkenyl is, for example, 3 to 7. Examples of the aforementioned cycloalkenyl include cyclopropenyl, cyclobutenyl, cyclopentenyl, cyclohexenyl, cycloheptenyl and the like. Among them, cyclopropenyl, cyclobutenyl, cyclopentenyl, cyclohexenyl, and the like are preferable. The aforementioned term "cycloalkenyl" also encompasses, for example, bridged cyclic hydrocarbon groups and Spiro hydrocarbon groups having an unsaturated bond in their rings.

In the present invention, examples of the "arylalkyl" include benzyl, 2-phenethyl, naphthalenylmethyl and the like. Examples of the "cycloalkylalkyl" and "cyclylalkyl" include cyclohexylmethyl adamantylmethyl and the like. Examples of the "hydroxyalkyl" include hydroxymethyl 2-hydroxyethyl and the like.

In the present invention, the "alkoxy" encompasses, for example, groups composed of any of the aforementioned alkyls and oxygen (alkyl-O-groups) and examples thereof include methoxy, ethoxy, n-propoxy, isopropoxy, n-butoxy and the like. Examples of the "alkoxyalkyl" include methoxymethyl and the like. Examples of the "aminoalkyl" include 2-aminoethyl and the like.

In the present invention, examples of the "heterocyclyl" include 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazolinyl, 2-imidazolinyl, 4-imidazolinyl, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperazinyl, 2-piperazinyl, piperazinone, 2-morpholinyl, 3-morpholinyl, morpholino, tetrahydropyranyl, tetrahydrofuranyl and the like.

In the present invention, examples of the "heterocyclylalkyl" include piperidinylmethyl, piperazinylmethyl and the like. Examples of the "heterocyclylalkenyl" include 2-piperidinylethenyl and the like. Examples of the "heteroarylalkyl" include pyridylmethyl, quinolin-3-ylmethyl and the like.

In the present invention, the term "silyl" encompasses groups represented by the chemical formula $R_3Si-$, where R independently can be selected from the aforementioned alkyls, aryls, and cycloalkyls. Examples of the silyl include a trimethylsilyl group, a tert-butyldimethylsilyl group and the like. Examples of the "silyloxy" include a trimethylsilyloxy group and the like. Examples of the "silyloxyalkyl" include trimethylsilyloxymethyl and the like.

In the present invention, examples of the "alkylene" include methylene, ethylene, propylene and the like.

In the present invention, the above-described various groups may be substituted. Examples of the aforementioned substituent include hydroxy, carboxy, sulfo, halogen, alkyl halide (haloalkyl, e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), cyclylalkyl, hydroxyalkyl (e.g., hydroxymethyl, hydroxyethyl), alkoxyalkyl (e.g., methoxymethyl, ethoxymethyl, ethoxyethyl), aryl (e.g., phenyl, naphthyl), arylalkyl (e.g., benzyl, phenethyl), alkylaryl (e.g., p-methylphenyl), heteroaryl (e.g., pyridyl, furyl), heteroarylalkyl (e.g., pyridylmethyl), heterocyclyl (e.g., piperidyl), heterocyclylalkenyl, heterocyclylalkyl (e.g., morpholylmethyl), alkoxy (e.g., methoxy, ethoxy, propoxy, butoxy), halogenated alkoxy (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino [alkylamino (e.g., methylamino, ethylamino, dimethylamino), acylamino (e.g., acetylamino, benzoylamino), arylalkylamino (e.g., benzylamino, tritylamino), hydroxyamino], aminoalkyl (e.g., aminomethyl), alkylaminoalkyl (e.g., diethylaminomethyl), carbamoyl, sulfamoyl, oxo, silyl, silyloxyalkyl and the like.

The artificial match-type miRNA of the present invention may include, for example, a labeling substance, and may be labeled with the aforementioned labeling substance. The aforementioned labeling substance is not particularly limited, and may be, for example, a fluorescent substance, a dye, an isotope, or the like. Examples of the aforementioned labeling substance include: fluorophores such as pyrene, TAMRA, fluorescein, a Cy3 dye, a Cy5 dye and the like. Examples of the aforementioned dye include Alexa dyes such as Alexa 488 and the like. Examples of the aforementioned isotope include stable isotopes and radioisotopes. Among them, stable isotopes are preferable. Moreover, for example, the aforementioned stable isotope does not change the physical properties of a compound labeled therewith and thus has an excellent property as a tracer. The aforementioned stable isotope is not particularly limited, and examples thereof include $^2$H, $^{13}$C, $^{15}$N, $^{17}$O, $^{18}$O, $^{33}$S, $^{34}$S and $^{36}$S.

As described above, the artificial match-type miRNA of the present invention can inhibit the aforementioned expression of a target gene. Thus, the artificial match-type miRNA of the present invention can be used, for example, as a therapeutic agent for treating a disease caused by a gene. When the artificial match-type miRNA of the present invention has a guide strand sequence of a mature miRNA that inhibits expression of a gene causing the aforementioned disease, for example, it is possible to treat the aforementioned disease by inhibiting the expression of the aforementioned target gene. In the present invention, the term "treatment" encompasses prevention of the aforementioned diseases; improvement of the diseases; and improvement in prognosis, for example, and it can mean any of them. The aforementioned disease is not particularly limited and, for example, the aforementioned sequence that suppresses expression can be set appropriately according to the object disease. Examples of the aforementioned disease include cancer such as breast cancer, lung cancer, stomach cancer, colorectal cancer, liver cancer, pancreatic cancer, esophageal cancer, prostate cancer, gallbladder cancer, uterine body cancer, uterus cervix cancer, ovarian cancer, osteosarcoma, leukemia and the like, and diseases such as lung fibrosis, hepatic fibrosis and the like.

The method of using the artificial match-type miRNA of the present invention is not particularly limited. For example, the aforementioned artificial match-type miRNA may be administered to a subject having the aforementioned target gene.

Examples of the aforementioned subject include cells, tissues and organs. Examples of the aforementioned subject also include humans, nonhuman animals such as nonhuman mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, COS cells and the like; stem cells such as ES cells, hematopoietic stem cells and the like; and cells isolated from living organisms, such as primary cultured cells and the like.

In the present invention, the aforementioned target gene whose expression is to be inhibited is not particularly limited, and any desired gene can be set to the target gene. As mentioned above, the aforementioned mature miRNA can be selected according to the kind of the aforementioned target gene.

As to the use of the artificial match-type miRNA of the present invention, the following description regarding the composition, the expression inhibitory method, the treatment method, and the like according to the present invention to be describe below can be referred to.

Since the artificial match-type miRNA of the present invention can inhibit the expression of a target gene as described above, for example, it is useful as a pharmaceutical product, a diagnostic agent, an agricultural chemical, and a tool for conducting research on agriculture, medical science, life science, and the like.

The method for synthesizing the artificial match-type miRNA of the present invention is not particularly limited, and a conventionally known production method of nucleic acid can be employed. Examples of the aforementioned synthesis method include synthesis methods according to genetic engineering procedures, chemical synthesis methods and the like. Examples of the genetic engineering procedures include: synthesis methods utilizing in vitro transcription; methods using a vector; methods carried out using a PCR cassette and the like. The aforementioned vector is not particularly limited, and examples thereof include non-virus vectors such as plasmid and the like, and virus vectors and the like. The aforementioned chemical synthesis methods are not particularly limited, and examples thereof include a phosphoramidite method, an H-phosphonate method and the like. The aforementioned chemical synthesis methods can be carried out, for example, using a commercially available automated nucleic acid synthesizer. In the aforementioned chemical synthesis methods, an amidite is generally used. The aforementioned amidite is not particularly limited. Examples of commercially available amidites include RNA Phosphoramidites (2'-O-TBDMSi, trade name, Samchully Pharm. Co., Ltd.), ACE amidite, TOM amidite, CEE amidite, CEM amidite, TEM amidite and the like.

(2) Composition

The expression inhibitory composition according to the present invention is, as described above, a composition for inhibiting the expression of a target gene, characteristically containing the aforementioned artificial match-type miRNA of the present invention. The composition of the present invention is characterized in that it contains the aforementioned artificial match-type miRNA of the present invention, and other configurations are by no means limited. The expression inhibitory composition of the present invention can also be referred to, for example, as an expression inhibitory reagent.

According to the present invention, for example, by administering to a subject in which the aforementioned target gene is present, it is possible to inhibit the expression of the aforementioned target gene.

Furthermore, as described above, the pharmaceutical composition according to the present invention characteristically contains the aforementioned artificial match-type miRNA of the present invention. The composition of the present invention is characterized in that it contains the aforementioned artificial match-type miRNA of the present invention, and other configurations are by no means limited. The pharmaceutical composition of the present invention can also be referred to, for example, as a pharmaceutical product.

According to the present invention, for example, administration to a patient with a disease caused by a gene can inhibit the expression of the aforementioned gene, thereby treating the aforementioned disease. In the present invention, the term "treatment" encompasses, as mentioned above, prevention of the aforementioned diseases; improvement of the diseases; and improvement in prognosis, for example, and it can mean any of them.

In the present invention, a disease to be treated is not particularly limited, and examples thereof include diseases caused by the expression of genes. Depending on the kind of the aforementioned disease, a gene that causes the disease may be set as the aforementioned target gene, and further, depending on the aforementioned target gene, the aforementioned guide strand sequence of the aforementioned mature miRNA may be selected.

The method of using the expression inhibitory composition and the pharmaceutical composition according to the present invention (hereinafter, both the compositions simply are referred to as "the compositions") are not particularly limited, and examples thereof include administering the aforementioned artificial match-type miRNA to a subject having the aforementioned target gene.

Examples of the aforementioned subject include cells, tissues, and organs. Examples of the aforementioned subject also include humans, nonhuman animals such as nonhuman mammals excluding humans. The aforementioned administration may be performed, for example, in vivo or in vitro. The aforementioned cells are not particularly limited, and examples thereof include: various cultured cells such as HeLa cells, 293 cells, NIH3T3 cells, COS cells and the like; stem cells such as ES cells, hematopoietic stem cells and the like; and cells isolated from living organisms, such as primary cultured cells and the like.

The aforementioned administration method is not particularly limited, and can be determined, for example, as appropriate depending on the subject. When the aforementioned subject is a cultured cell, the administration method may be, for example, a method using a transfection reagent, an electroporation method, or the like.

For example, each of the compositions of the present invention may contain only the artificial match-type miRNA of the present invention or further may contain an additive(s) in addition to the artificial match-type miRNA. The aforementioned additive is not particularly limited, and is preferably, for example, a pharmaceutically acceptable additive. The kind of the aforementioned additive is not particularly limited, and can be selected as appropriate depending on, for example, the kind of the subject.

In the composition of the present invention, for example, the aforementioned artificial match-type miRNA may form a complex with the aforementioned additive. The aforementioned additive can also be referred to, for example, as a complexing agent. The aforementioned complex formation allows, for example, the aforementioned artificial match-type miRNA to be delivered efficiently.

The aforementioned complexing agent is not particularly limited, and examples thereof include polymers, cyclodextrins, adamantine and the like. Examples of the aforementioned cyclodextrins include linear cyclodextrin copolymers, linear oxidized cyclodextrin copolymers and the like.

Other examples of the aforementioned additive include a carrier, a binding substance that binds to a target cell, a condensing agent, a fusogenic agent, an excipient and the like.

(3) Expression Inhibitory Method

The expression inhibitory method according to the present invention is, as described above, a method for inhibiting the expression of a target gene, in which the aforementioned artificial match-type miRNA of the present invention is characteristically used. The expression inhibitory method of the present invention is characterized in that the aforementioned artificial match-type miRNA of the present invention is used therein, and other steps and conditions are by no means limited.

In the expression inhibitory method of the present invention, the mechanism by which the aforementioned target gene expression is inhibited is not particularly limited, and examples thereof include inhibition of the expression by mature miRNA.

The expression inhibitory method of the present invention includes, for example, the step of administering the aforementioned artificial match-type miRNA to a subject in which the aforementioned target gene is present. By the aforementioned administration step, for example, the aforementioned artificial match-type miRNA is brought into contact with the aforementioned subject. Examples of the aforementioned subject include cells, tissues, and organs. Examples of the aforementioned subject also include humans, nonhuman animals such as nonhuman mammals excluding humans. The aforementioned administration may be performed, for example, in vivo or in vitro.

In the expression inhibitory method of the present invention, for example, the aforementioned artificial match-type miRNA alone may be administered, or the aforementioned composition of the present invention containing the aforementioned artificial match-type miRNA may be administered. The aforementioned administration method is not particularly limited and, for example, can be selected as appropriate depending on the kind of the subject.

(4) Treatment Method

As described above, the method for treating a disease according to the present invention includes the step of administering the aforementioned artificial match-type miRNA of the present invention to a patient, and is characterized in that the aforementioned guide strand sequence in the aforementioned artificial match-type miRNA is the guide strand sequence of a mature miRNA that inhibits expression of a gene causing the aforementioned disease. The treatment method of the present invention is characterized by the use of the aforementioned artificial match-type miRNA of the present invention, and other steps and conditions are by no means limited.

The aforementioned expression inhibitory method of the present invention also applies to, for example, the treatment method of the present invention. The aforementioned administration method is not particularly limited and may be, for example, any of oral administration and parenteral administration.

(5) Use of Artificial Match-Type miRNA

The use according to the present invention is the use of the aforementioned artificial match-type miRNA of the present invention for the aforementioned inhibition of the expression of a target gene.

The single strand nucleic acid according to the present invention is a single strand nucleic acid for use in the treatment of a disease. The aforementioned single strand nucleic acid is the aforementioned artificial match-type miRNA of the present invention, and is characterized in that the aforementioned guide strand sequence in the aforementioned artificial match-type miRNA is the guide strand sequence of a mature miRNA that inhibits expression of a gene causing the aforementioned disease.

In the following, the present invention will be described in detail with reference to examples and the like. It is to be noted, however, the present invention is by no means limited thereto.

EXAMPLES

Example 1

The artificial match-type miRNA of the present invention was synthesized based on the guide strand of a mature miR-34a, and suppression of the growth of H1299 cells was confirmed.

(1) Synthesis of miRNA

As miRNA of a positive control, human mature miR-34a composed of the guide strand (SEQ ID NO: 1) and the passenger strand (SEQ ID NO: 6) shown below was synthesized. As a negative control, mature miR-34a scramble composed of the guide strand scramble (SEQ ID NO: 7), wherein the base composition of the aforementioned guide strand is scrambled, and the corresponding passenger strand (SEQ ID NO: 8) was synthesized.

As the artificial match-type miRNA in the Examples, match-type miR-34a, wherein X region composed of the aforementioned guide strand (SEQ ID NO: 1) and an additional sequence, and Y region composed of a sequence completely complementary to the aforementioned X region and an overhang, are linked via a non-nucleotide structure (shown by [P] in the sequences) of a proline derivative of the following formula, was synthesized. In the following sequences, the underlined part corresponds to the aforementioned guide strand. The aforementioned non-nucleotide structure in the aforementioned match-type miRNA is shown by the following formula and introduced using L-prolinediamideamidite (see WO 2012/017919) in the aforementioned synthesis of match-type miRNA. In addition, as a negative control to the artificial match-type miRNA, match-type miR-34a scramble composed of the aforementioned guide strand wherein the base composition of the guide strand is scrambled, and a passenger strand corresponding thereto was synthesized.

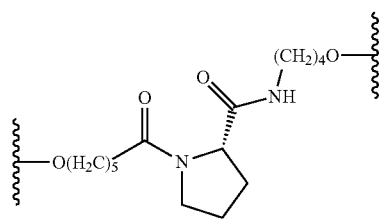

The sequences and structures of these miRNAs are shown below. In the following, the sequences shown by underlined parts correspond to the guide strands.

```
mature miR-34a
guide strand
                                         (SEQ ID NO: 1)
5'-UGGCAGUGUCUUAGCUGGUUGU-3' passenger strand
                                         (SEQ ID NO: 6)
5'-CAAUCAGCAAGUAUACUGCCCU-3' mature miR-34a scramble
guide strand
                                         (SEQ ID NO: 7)
5'-UGUAUCGUUAUCGGGUCGGUUG-3' passenger strand
                                         (SEQ ID NO: 8)
5'-CAACCGACCCGAUAACGAUACA-3' match-type miR-34a
                                         (SEQ ID NO: 9)
5'-UGGCAGUGUCUUAGCUGGUUGUUCC-[P]-

GGAACAACCAGCUAAGACACUGCCAUA-3' match-type miR-34a scramble
                                         (SEQ ID NO: 10)
5'-UGUAUCGUUAUCGGGUCGGUUGUCC-[P]-

GGACAACCGACCCGAUAACGAUACAUA-3' mature miR-34a

U   G CU A    G   U              (SEQ ID NO: 1)
  GGCAGU U  U GCUG UUG
  ||||||   |  ||||  |||
  CCGUCA A  A CGAC AAC               (SEQ ID NO: 6)
 UC     U UG A    U
match-type miR-34a
 UGGCAGUGUCUUAGCUGGUUGUUCC           (SEQ ID NO: 9)
 |||||||||||||||||||||||||    P
 AUACCGUCACAGAAUCGACCAACAAGG
```

(2) Influence of Artificial Match-Type miRNA on Cell Derived from Lung Cancer

The aforementioned artificial match-type miRNA was introduced into human non-small cell type lung cancer cell line (NCI-H1299) and an influence on the aforementioned cells was confirmed.

(2-1) Transfection

The aforementioned miRNA was dissolved in distilled water for injection (Otsuka Pharmaceutical Co., Ltd., hereinafter the same) to prepare 100 μmol/L miRNA solution. As the medium, RPMI-Medium 1640 (Invitrogen) containing 10% FBS was used. The culture conditions were set to 37° C., 5% $CO_2$.

First, the cells were cultured in the aforementioned medium, and the cultured solution was dispensed to a 24-well plate so that each well contained 500 μL of the cultured solution to achieve a density of $1\times10^4$ cells/well. The cells in the aforementioned wells were cultured for 24 hours. The cells were transfected with the aforementioned miRNA using a transfection reagent RNAi MAX Transfection Reagent (trade name, Life Technologies) according to the attached protocol. The transfection was carried out by setting the composition per well as follows. In the following composition, (B) is Opti-MEM (trade name, Life Technologies), (C) is the aforementioned RNA solution, and 49 μL in total of them was added. The final concentration of the aforementioned miRNA in the aforementioned well was set to 100 nmol/L. After the transfection, the cells in the aforementioned well were cultured for 3 days. After the aforementioned culture for 3 days, the cultured cells were confirmed as shown below.

TABLE 1

| (composition per well: μL) | |
|---|---|
| cultured solution | 450 |
| (A) transfection reagent | 1 |
| (B) + (C) | 49 |
| | 500 |

(2-2) Count of Cell Number

Figure 2:
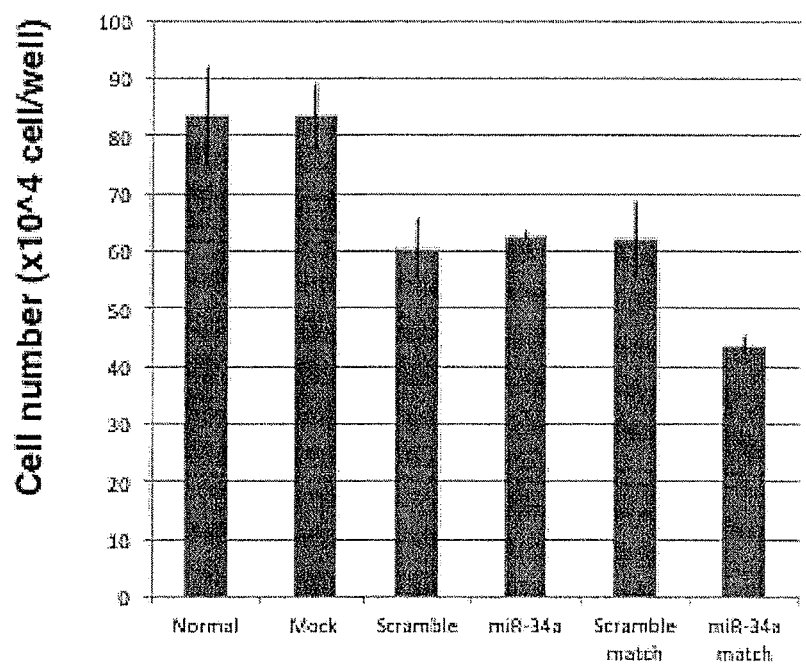
FIG. 2 is a graph showing the number of cells per well in Example 1 of the present invention.

The cell number per well of cultured cells was counted after culture. The results are shown in FIG. 2. FIG. 2 is a graph showing cell number per well. In FIG. 2, "Normal" shows the results of untreated cells, "Mock" shows cells introduced with a transfection reagent alone, "Scramble" shows miR-34a scramble as a negative control, "miR-34a" shows mature miR-34a as a positive control, "Scramble match" shows match-type miR-34a scramble as a negative control, and "miR-34a match" shows match-type miR-34a in the Examples (hereinafter the same). As shown in FIG. 2, the match-type miR-34a in the Examples could decrease the cell number to the same level as the positive control mature miR-34a.

(2-3) MTT Assay

Figure 3:
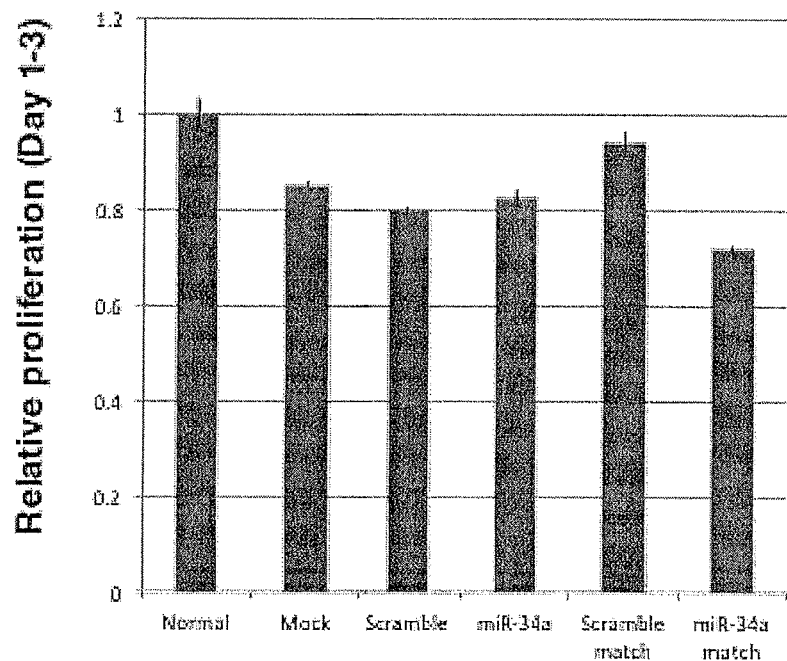
FIG. 3 is a graph showing the relative values of cell proliferation in Example 1 of the present invention.

After culture, the cultured cells were subjected to MTT assay by using a commercially available reagent kit (trade name Cell Count Reagent SF, Nacalai Tesque), and cell proliferation was evaluated. Evaluation of cell proliferation was shown in relative values based on the results of Normal (non-treatment) as 1. The results are shown in FIG. 3. FIG. 3 is a graph showing the relative value of cell proliferation. As shown in FIG. 3, the match-type miR-34a in the Examples could decrease the cell number to the same level as the positive control mature miR-34a.

(2-4) Apoptosis

Figure 4:
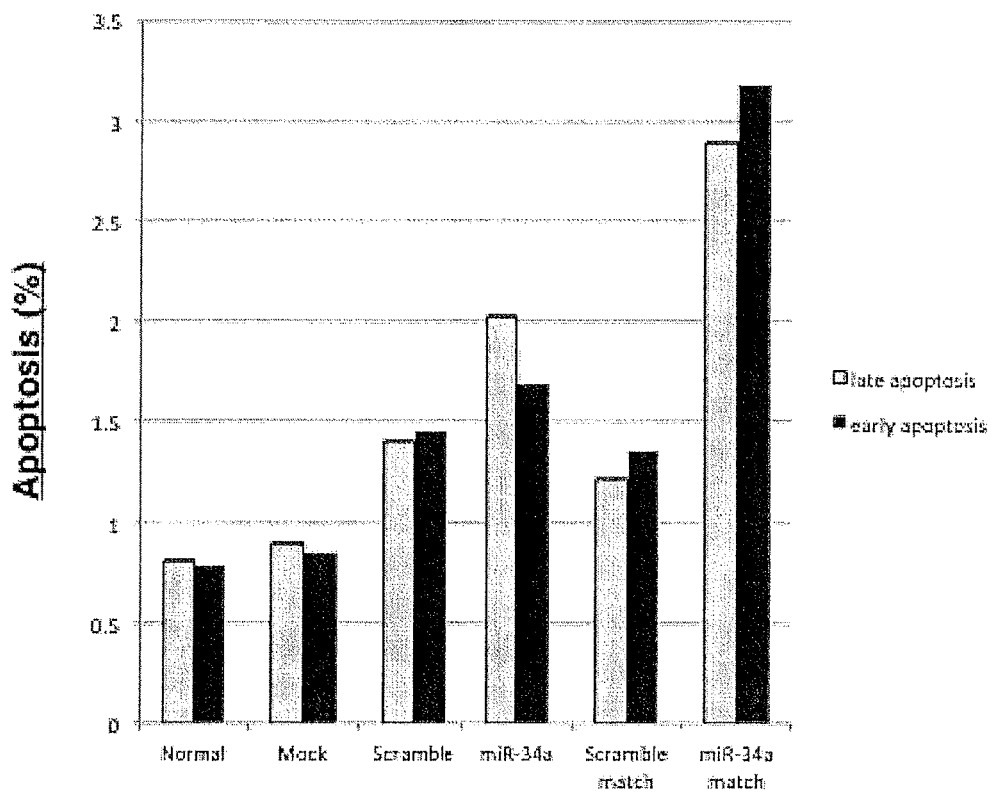
FIG. 4 is a graph showing the proportion of apoptosis in Example 1 of the present invention.

After culture, the cultured cells were subjected to the detection of apoptosis by using a commercially available reagent kit (trade name Annexin V:PE Apoptosis Detection Kit, BD Biosciences). The results are shown in FIG. 4. FIG. 4 is a graph showing early stage apoptosis (%) and the latter stage apoptosis (%). As shown in FIG. 4, the match-type miR-34a in the Examples could promote apoptosis to the same level as the positive control mature miR-34a.

(2-5) Suppression of Expression of mRNA

RNA was recovered from the cultured cells after culture, by using ISOGEN reagent (trade name, NIPPON GENE) according to the attached protocol.

Then, using reverse transcriptase (trade name M-MLV reverse transcriptase, Invitrogen) according to the attached protocol, cDNA was synthesized from the aforementioned RNA. Quantitative PCR was carried out using the aforementioned synthesized cDNA as a template, and the amounts of AXL cDNA and MET cDNA were measured. The cDNA amount thereof was also measured using GAPDH cDNA as an internal control.

In the aforementioned quantitative PCR, FastStart Universal SYBR Green Master (trade name, Roche) was used as a reagent, MX3000P (trade name, Stratagene) was used as a thermocycler, and MxPro (trade name, Stratagene) was used as an analysis instrument (hereinafter the same). For amplification of the aforementioned AXL cDNA, the aforementioned MET cDNA and the aforementioned GAPDH cDNA, the following primer sets were used. The total amount of the reaction mixture was 25 μL, and the measurement was performed 3 times for each.

```
AXL primer set
                                          (SEQ ID NO: 11)
5'-CTCAACCAGGACGACTCCAT-3'

(SEQ ID NO: 12)
5'-AGACCGCTTCACTCAGGAAA-3'

MET primer set
                                          (SEQ ID NO: 13)
5'-CAGGCAGTGCAGCATGTAGT-3'

(SEQ ID NO: 14)
5'-TGTCCAACAAAGTCCCATGA-3'

GAPDH primer set
                                          (SEQ ID NO: 15)
5'-ATGGGGAAGGTGAAGGTCG-3'

(SEQ ID NO: 16)
5'-GGGTCATTGATGGCAACAATATC-3'
```

Figure 5:
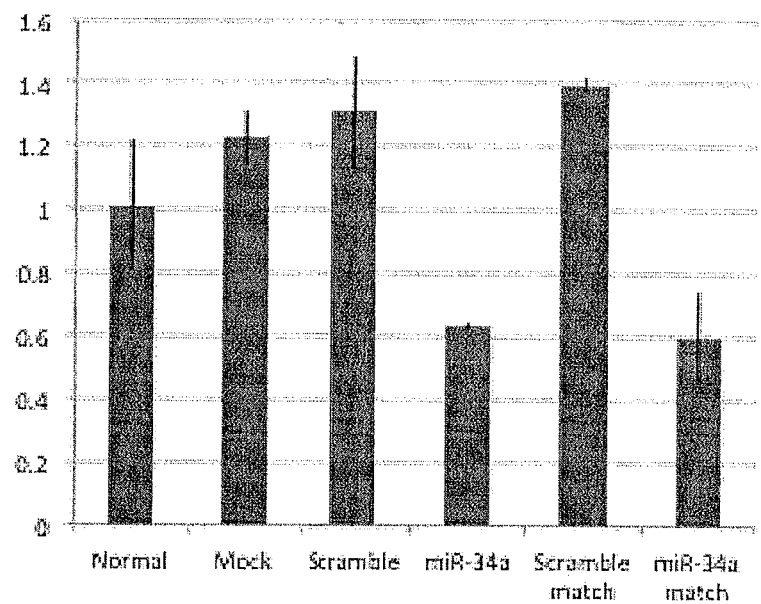
FIGS. 5(A) and 5(B) are graphs showing the relative values of AXL mRNA amount (FIG. 5(A)) and MET mRNA amount (FIG. 5(B)) in Example 1 of the present invention.
Figure 5:
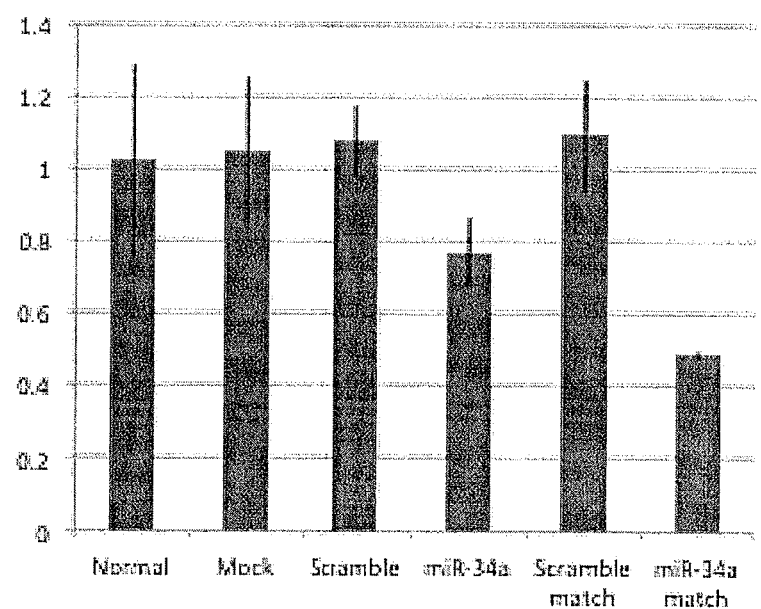

Relative values of AXL mRNA and MET mRNA in each transfected cell, when AXL mRNA or MET mRNA in miRNA non-added control is 1, were calculated. The results thereof are shown in FIG. 5. FIG. 5(A) shows the results of AXL mRNA, and FIG. 5(B) shows the results of MET mRNA.

As shown in FIG. 5, the match-type miR-34a in the Examples decreased the amount of AXL mRNA and the amount of MET mRNA to the same level as the positive control mature miR-34a. Therefore, it can be said that the translation of proteins encoded by AXL mRNA and MET mRNA is suppressed by the aforementioned artificial match-type miRNA.

From these results, it was found that the match-type miR-34a in the Examples can suppress expression of AXL mRNA and MET mRNA and the like, and enables suppression of the growth of H1299 cells and promotion of apoptosis.

Different from double stranded mature miR-34a, since the aforementioned artificial match-type miRNA is a single strand nucleic acid molecule, it does not require annealing of each single strand when in use and can avoid recognition by TLR3 and the like involved in natural immunity.

Example 2

In match-type miR-34a of Example 1, the additional sequence of X region and the overhang of Y region were shortened.

(1) Synthesis of miRNA

As shown below, match-type miR-34a has a 3 base-length additional sequence (J) enclosed in rectangle on the 3'-side of the X region, and a 2 base-length overhang (O) enclosed in rectangle on the 5'-side of the Y region. Therefore, a molecule wherein the aforementioned additional sequence was deleted by 1 base from the 3'-side and the sequence corresponding thereto on the Y region side was deleted by 1 base from the 5'-side; a molecule wherein the overhang was deleted by 1 base from the 3'-side; and a molecule wherein the aforementioned additional sequence and the overhang were deleted by 1 base were synthesized, and suppression of the expression of AXL mRNA and MET mRNA was confirmed in the same manner as in the aforementioned Example 1. In the following sequences, the 5'-side region of [P] is X region; in the aforementioned X region, the underlined part is the aforementioned guide strand sequence, the rest is the aforementioned additional sequence, and the 3'-side region of [P] is Y region; and in the aforementioned Y region, the region enclosed in rectangle is the overhang.

```
match-type miR-34a
```
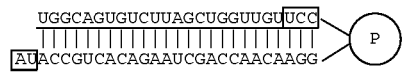
```
    UGGCAGUGUCUUAGCUGGUUGU UCC              (SEQ ID NO: 9)
    ||||||||||||||||||||||    ⎤
    AU ACCGUCACAGAAUCGACCAACAAGG       P
```

```
        match-type miR-34a
        O2J3
                                            (SEQ ID NO: 9)
        5'-UGGCAGUGUCUUAGCUGGUUGUUCC-[P]-
        GGAACAACCAGCUAAGACACUGCCA UA -3'

O2J2
                                            (SEQ ID NO: 17)
        5'-UGGCAGUGUCUUAGCUGGUUGUUC-[P]-
        GAACAACCAGCUUAAGACACUGCCA UA -3'

O2J1
                                            (SEQ ID NO: 18)
        5'-UGGCAGUGUCUUAGCUGGUUGUU-[P]-
        AACAACCAGCUAAGACACUGCCA UA -3'

O2J0
                                            (SEQ ID NO: 19)
        5'-UGGCAGUGUCUUAGCUGGUUGU-[P]-
        ACAACCAGCUAAGACACUGCCA UA -3'

O1J3
                                            (SEQ ID NO: 20)
        5'-UGGCAGUGUCUUAGCUGGUUGUUCC-[P]-
        GGAACAACCAGCUAAGACACUGCCA U -3'

O1J2
                                            (SEQ ID NO: 21)
        5'-UGGCAGUGUCUUAGCUGGUUGUUC-[P]-
        GAACAACCAGCUAAGACACUGCCA U -3'

O1J1
                                            (SEQ ID NO: 22)
        5'-UGGCAGUGUCUUAGCUGGUUGUU-[P]-
        AACAACCAGCUAAGACACUGCCA U -3'

O1J0
                                            (SEQ ID NO: 23)
        5'-UGGCAGUGUCUUAGCUGGUUGU-[P]-
        ACAACCAGCUAAGACACUGCCA U -3'

O0J3
                                            (SEQ ID NO: 24)
        5'-UGGCAGUGUCUUAGCUGGUUGUUCC-[P]-
        GGAACAACCAGCUAAGACACUGCCA-3'

O0J2
                                            (SEQ ID NO: 25)
        5'-UGGCAGUGUCUUAGCUGGUUGUUC-[P]-
        GAACAACCAGCUAAGACACUGCCA-3'

O0J1
                                            (SEQ ID NO: 26)
        5'-UGGCAGUGUCUUAGCUGGUUGUU-[P]-
        AACAACCAGCUAAGACACUGCCA-3'

O0J0
                                            (SEQ ID NO: 27)
        5'-UGGCAGUGUCUUAGCUGGUUGU-[P]-
        ACAACCAGCUAAGACACUGCCA-3'
```

Figure 6:
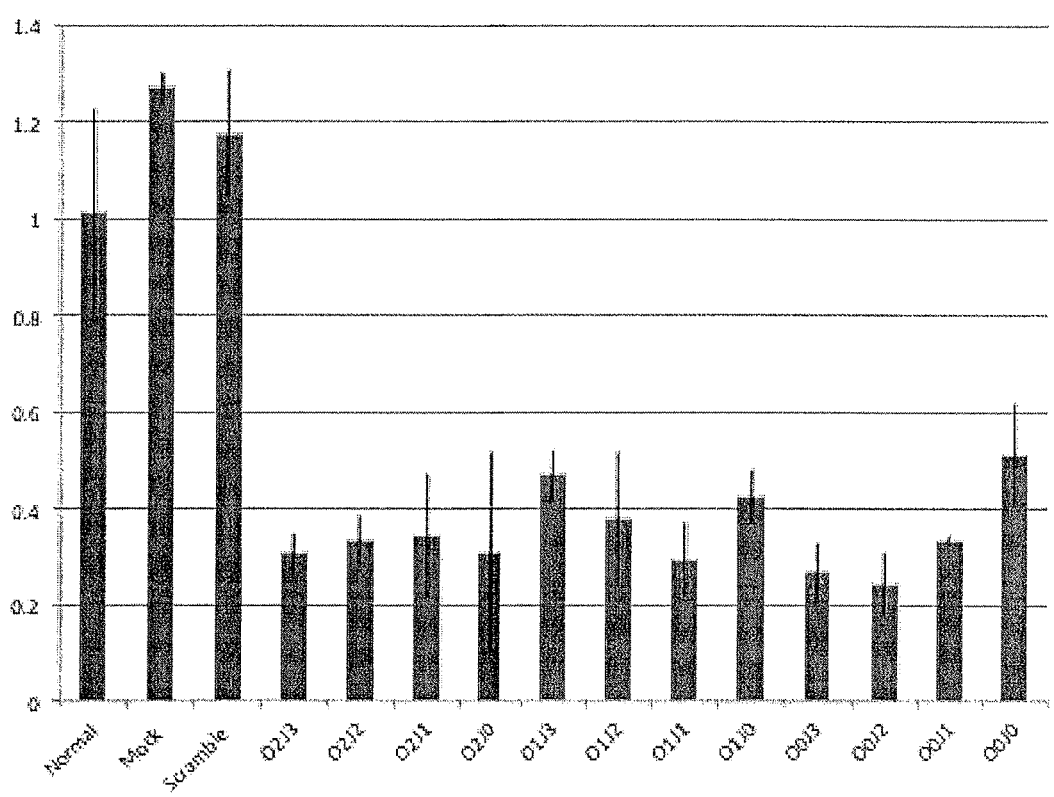
FIG. 6 is a graph showing the relative values of AXL mRNA amount in Example 2 of the present invention.
Figure 7:
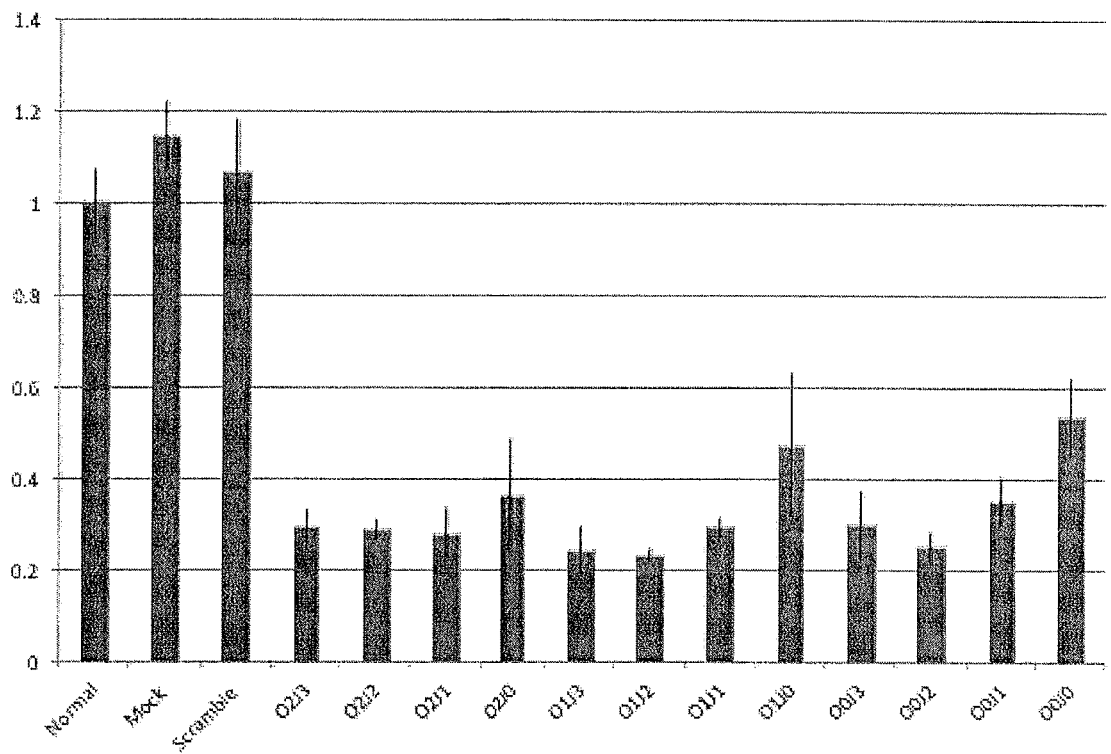
FIG. 7 is a graph showing the relative values of MET mRNA amount in Example 2 of the present invention.

The results are shown in FIG. 6 and FIG. 7. FIG. 6 shows the results of AXL mRNA, and FIG. 7 shows the results of MET mRNA. As shown in FIG. 6 and FIG. 7, the expression suppressive effect was maintained even when the additional sequence of the aforementioned X region and the overhang of the aforementioned Y region were shortened.

Example 3

In match-type miR-34a, the non-nucleotide structure of the linker was altered and the additional sequence of X region was increased or decreased, and a suppressive effect on the expression of AXL mRNA and MET RNA was examined.

(1) Synthesis of miRNA

As shown below, match-type miR-34a(PH-0039), wherein the base sequence of the overhang region is altered from that of match-type miR-34a of Example 1, was synthesized. Furthermore, a molecule wherein the additional sequence of PH-0039 and a sequence corresponding thereto on the Y region side were deleted (PH-0037), and a molecule wherein an additional sequence and a sequence corresponding thereto on the Y region side were extended to 5 bases length (PH-0093) was synthesized.

Also, molecules wherein the linker regions of PH-0037, PH-0039 and PH-0093 are substituted by a non-nucleotide structure (shown by [TP] in sequences) in the terephthalic acid derivative of the following formula were synthesized (XH-0016, XH-0025 and XH-0027, respectively). The non-nucleotide structure was introduced by using terephthalic acid amidite (see WO 2013/133221).

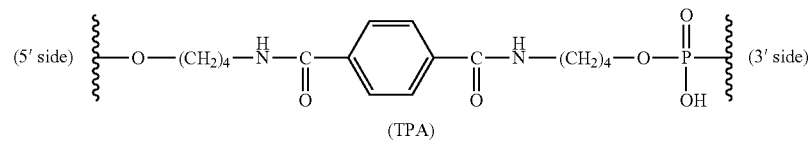
(TPA)

Molecules wherein the linker regions of PH-0037 and PH-0039 are substituted by a non-nucleotide structure (shown by [Gly] in sequences) in the glycine derivative of the following formula (XH-0012 and XH-0028, respectively), and

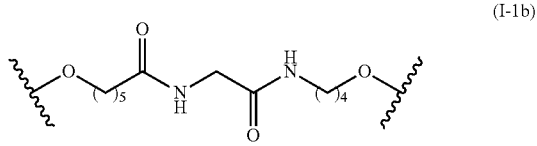
(I-1b)

molecules wherein the linker regions of PH-0037 and PH-0039 are substituted by a non-nucleotide structure (shown by [GlyGly] in sequences) in the glycylglycine derivative of the following formula (XH-0014 and XH-0029, respectively).

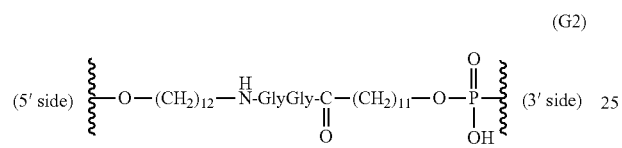
(G2)

GlyGly in the aforementioned chemical formula (G2) is an atomic group represented by the following chemical formula (GlyGly), wherein the terminal carbonylcarbon is bonded to N atom in the above-mentioned chemical formula (G2), and the terminal nitrogen atom in the following chemical formula (GlyGly) is bonded to carbonylcarbon in the above-mentioned chemical formula (G2).

(GlyGly) —HN—CH$_2$—CO—HN—CH$_2$—CO—

Also, molecules wherein the linker regions of PH-0037 and PH-0039 are substituted by a non-nucleotide structure (shown by [K] in sequences) in the lysine derivative of the following formula (KH-0007 and KH-0011, respectively) were synthesized.

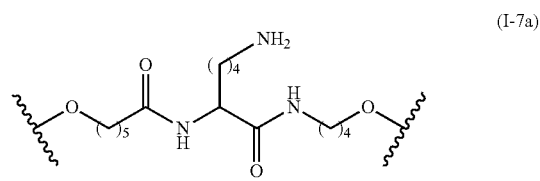
(I-7a)

The non-nucleotide structure of the aforementioned glycine derivative was introduced by using glycine amideamidite (see WO 2013/103146), the non-nucleotide structure of the aforementioned glycylglycine derivative was introduced by using glycylglycine amideamidite (see WO 2013/133221), and the non-nucleotide structure of the lysine derivative was introduced by using L-lysinamideamidite (see WO 2013/103146).

```
                    (SEQ ID NO: 28)                           (SEQ ID NO: 28)
        PH-0037                               XH-0016
        UGGCAGUGUCUUAGCUGGUUGU                UGGCAGUGUCUUAGCUGGUUGU
                                P                                      TP
        UCACCGUCACAGAAUCGACCAACA              UCACCGUCACAGAAUCGACCAACA (SEQ ID NO: 29)                           (SEQ ID NO: 29)
        PH-0039                               XH-0025
        UGGCAGUGUCUUAGCUGGUUGUUCC             UGGCAGUGUCUUAGCUGGUUGUUCC
                                P                                      TP
        UCACCGUCACAGAAUCGACCAACAAGG           UCACCGUCACAGAAUCGACCAACAAGG (SEQ ID NO: 30)                           (SEQ ID NO: 30)
        PH-0093                               XH-0027
        UGGCAGUGUCUUAGCUGGUUGUUCCGG           UGGCAGUGUCUUAGCUGGUUGUUCCGG
                                P                                      TP
        UCACCGUCACAGAAUCGACCAACAAGGCC         UCACCGUCACAGAAUCGACCAACAAGGCC (SEQ ID NO: 28)                           (SEQ ID NO: 29)
        XH-0012                               XH-0028
        UGGCAGUGUCUUAGCUGGUUGU                UGGCAGUGUCUUAGCUGGUUGUUCC
                              Gly                                    Gly
        UCACCGUCACAGAAUCGACCAACA              UCACCGUCACAGAAUCGACCAACAAGG (SEQ ID NO: 28)                           (SEQ ID NO: 29)
        XH-0014                               XH-0029
        UGGCAGUGUCUUAGCUGGUUGU                UGGCAGUGUCUUAGCUGGUUGUUCC
                            GlyGly                                 GlyGly
        UCACCGUCACAGAAUCGACCAACA              UCACCGUCACAGAAUCGACCAACAAGG (SEQ ID NO: 28)                           (SEQ ID NO: 29)
        KH-0007                               KH-0011
        UGGCAGUGUCUUAGCUGGUUGU                UGGCAGUGUCUUAGCUGGUUGUUCC
                                K                                      K
        UCACCGUCACAGAAUCGACCAACA              UCACCGUCACAGAAUCGACCAACAAGG
```

In the following sequences, the 5'-side region of each linker is X region; in the aforementioned X region, the underlined part is the aforementioned guide strand sequence, the rest is the aforementioned additional sequence, and the 3'-side region of each linker is Y region.

PH-0037
(SEQ ID NO: 28)
5'-<u>UGGCAGUGUCUUAGCUGGUUGU</u>-[P]-

ACAACCAGCUAAGACACUGCCACU-3'

PH-0039
(SEQ ID NO: 29)
5'-<u>UGGCAGUGUCUUAGCUGGUUGU</u>UCC-[P]-

GGAACAACCAGCUAAGACACUGCCACU-3'

PH-0093
(SEQ ID NO: 30)
5'-<u>UGGCAGUGUCUUAGCUGGUUGU</u>UCCGG-[P]-

CCGGAACAACCAGCUAAGACACUGCCACU-3'

XH-0016
(SEQ ID NO: 28)
5'-<u>UGGCAGUGUCUUAGCUGGUUGU</u>-[TP]-

ACAACCAGCUAAGACACUGCCACU-3'

XH-0025
(SEQ ID NO: 29)
5'-<u>UGGCAGUGUCUUAGCUGGUUGU</u>UCC-[TP]-

GGAACAACCAGCUAAGACACUGCCACU-3'

XH-0027
(SEQ ID NO: 30)
5'-<u>UGGCAGUGUCUUAGCUGGUUGU</u>UCCGG-[TP]-

CCGGAACAACCAGCUAAGACACUGCCACU-3'

XH-0012
(SEQ ID NO: 28)
5'-<u>UGGCAGUGUCUUAGCUGGUUGU</u>-[Gly]-

ACAACCAGCUAAGACACUGCCACU-3'

XH-0028
(SEQ ID NO: 29)
5'-<u>UGGCAGUGUCUUAGCUGGUUGU</u>UCC-[Gly]-

GGAACAACCAGCUAAGACACUGCCACU-3'

XH-0014
(SEQ ID NO: 28)
5'-<u>UGGCAGUGUCUUAGCUGGUUGU</u>-[GlyGly]-

ACAACCAGCUAAGACACUGCCACU-3'

XH-0029
(SEQ ID NO: 29)
5'-<u>UGGCAGUGUCUUAGCUGGUUGU</u>UCC-[GlyGly]-

GGAACAACCAGCUAAGACACUGCCACU-3'

KH-0007
(SEQ ID NO: 28)
5'-<u>UGGCAGUGUCUUAGCUGGUUGU</u>-[K]-

ACAACCAGCUAAGACACUGCCACU-3'

KH-0011
(SEQ ID NO: 29)
5'-<u>UGGCAGUGUCUUAGCUGGUUGU</u>UCC-[K]-

GGAACAACCAGCUAAGACACUGCCACU-3'

As a negative control, match-type miRNA (PH-0000) comprising a guide strand composed of a sequence free of complementarity to all sequences recorded on nucleic acid databases and a passenger strand corresponding thereto was synthesized.

PH-0000
(SEQ ID NO: 31)
5'-<u>UACUAUUCGACACGCGAAGUU</u>CC-[P]-

GGAACUUCGCGUGUCGAAUAGUAUU-3'

As a positive control, a molecule wherein the guide strand of a mature miR-34a and a passenger strand are linked via a loop region of natural type pre-miRNA (NM-0004) and a double stranded match-type RNA wherein the guide strand of a mature miRNA and a sequence completely complementary thereto are annealed (NI-0209) were synthesized.

NM-0004 (64 mer) (SEQ ID NO: 35)

```
   U         A          -GUGA A
 GGCAGUGU-CUU GCUGGUUGU     GC
                              A
 CCGUCAUA GAA-CGACUAACGA    UG U
UC        *              AGGAA* A
  *      *       *    *
```

NI-0209 (22/22 mer)

UGGCAGUGUCUUAGCUGGUUGU (SEQ ID NO: 2)
UCACCGUCACAGAAUCGACCAA (SEQ ID NO: 34)

NM-0004
(SEQ ID NO: 32)
5'-<u>UGGCAGUGUCUUAGCUGGUUGU</u>UGUGAGCAAU

AGUAAGGAAGCAAUCAGCAAGUAUACUGCCCU-3'

NI-0209
guide strand (SEQ ID NO: 1)/
passenger strand (SEQ ID NO: 33)
5'-<u>UGGCAGUGUCUUAGCUGGUUGU</u>-3'/

5'-AACCAGCUAAGACACUGCCACU-3'

(2) Measurement of Expression Level of AXL Gene

Each of the aforementioned RNAs was dissolved in distilled water for injection (Otsuka Pharmaceutical Co., Ltd.) at 4 µmol/L, whereby an RNA solution was prepared.

H1299 cells (ATCC) were used as the cell. As the medium, RPMI Medium 1640 (Life Technologies) containing 10% FBS was used. The culture conditions were set to 37° C., 5% $CO_2$.

First, the cells were cultured in the aforementioned medium, and the cultured solution was dispensed to a 24-well plate so that each well contained 400 µL of the cultured solution to achieve a density of 4×104 cells/well. The cells were transfected with the aforementioned RNA using a transfection reagent Lipofectamine RNAiMAX (Life Technologies) according to the protocol attached to the aforementioned transfection reagent. Specifically, the transfection was carried out by setting the composition per well as follows. In the following composition, (B) is Opti-MEM (Life Technologies), (C) is the aforementioned 4 µmol/L RNA solution, 98.5 µL in total of them was added. The final concentration of the aforementioned RNA in the aforementioned well was set to 2 nmol/L.

TABLE 2

| (composition per well: μL) | |
|---|---|
| cultured solution | 450 |
| (A) transfection reagent | 1 |
| (B) + (C) | 49 |
| | 500 |

After the transfection, the cells in the aforementioned wells were cultured for 24 hours, and then, the RNA was collected using an RNeasy Mini Kit (Qiagen, Netherlands) according to the protocol supplied therewith. Subsequently, cDNA was synthesized from the aforementioned RNA by using Transcriptor First Strand cDNA Synthesis Kit (Roche) according to the protocol supplied therewith. Then, as shown below, PCR was carried out using the aforementioned synthesized cDNA as a template, and the expression levels of the AXL and MET genes and that of GAPDH gene as an internal standard were measured. The aforementioned expression levels of the AXL and MET genes were normalized with reference to that of the GAPDH gene mentioned above.

The aforementioned PCR was carried out using LightCycler 480 SYBR Green I Master (trade name, Roche) as a reagent and LightCycler 480 Instrument II (trade name, Roche) as an instrument (hereinafter the same). The aforementioned AXL, MET and GAPDH genes were amplified using the following primer sets, respectively.

```
PCR primer set for AXL gene
                            (SEQ ID NO: 11)
5'-CTCAACCAGGACGACTCCAT-3'

(SEQ ID NO: 12)
5'-AGACCGCTTCACTCAGGAAA-3'

PCR primer set for MET gene
                            (SEQ ID NO: 13)
5'-CAGGCAGTGCAGCATGTAGT-3'

(SEQ ID NO: 14)
5'-TGTCCAACAAAGTCCCATGA-3' primer set for GAPDH gene
                            (SEQ ID NO: 15)
5'-ATGGGGAAGGTGAAGGTCG-3'

(SEQ ID NO: 16)
5'-GGGTCATTGATGGCAACAATATC-3'
```

As control 1, regarding the cells to which 100 μL of the aforementioned solution (B) alone had been added to the aforementioned cultured solution, the expression levels of the genes also were measured (−). Furthermore, as control 2, regarding the cells subjected to the same transfection procedures as in the above except that the aforementioned RNA solution was not added and that the aforementioned (B) and 1.5 μL of the aforementioned (A) were added so that the total amount of (A) and (B) would be 100 μL, the expression level of the gene also was measured (mock).

As for the expression levels of normalized AXL and MET genes, the relative value of the expression level in the cell introduced with each RNA was determined based on the expression level in the cells of the control (mock) as 1.

(3) Results

Figure 8:
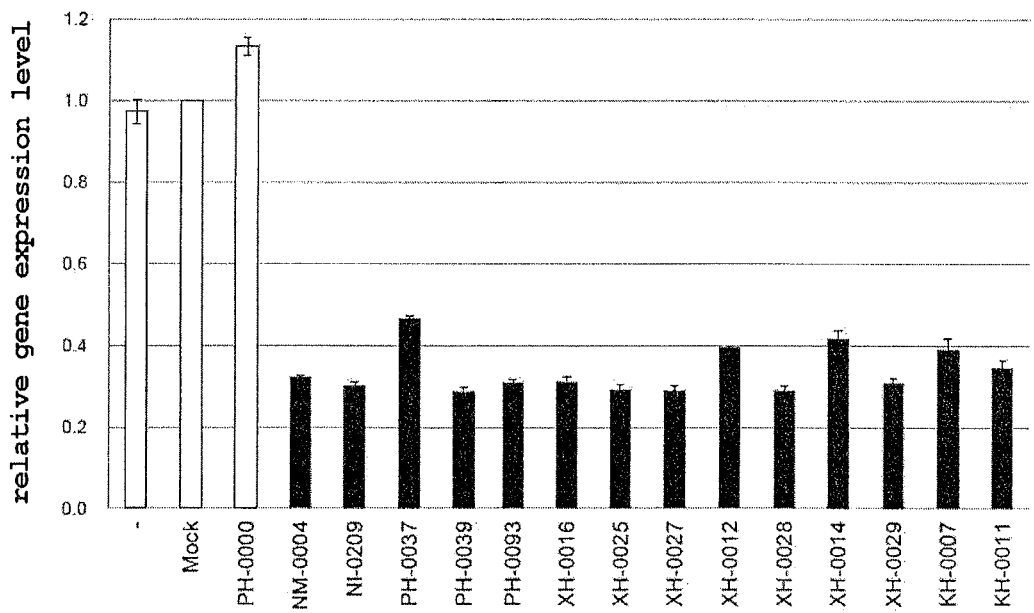
FIG. 8 is a graph showing the relative values of AXL mRNA amount in Example 3 of the present invention.
Figure 9:
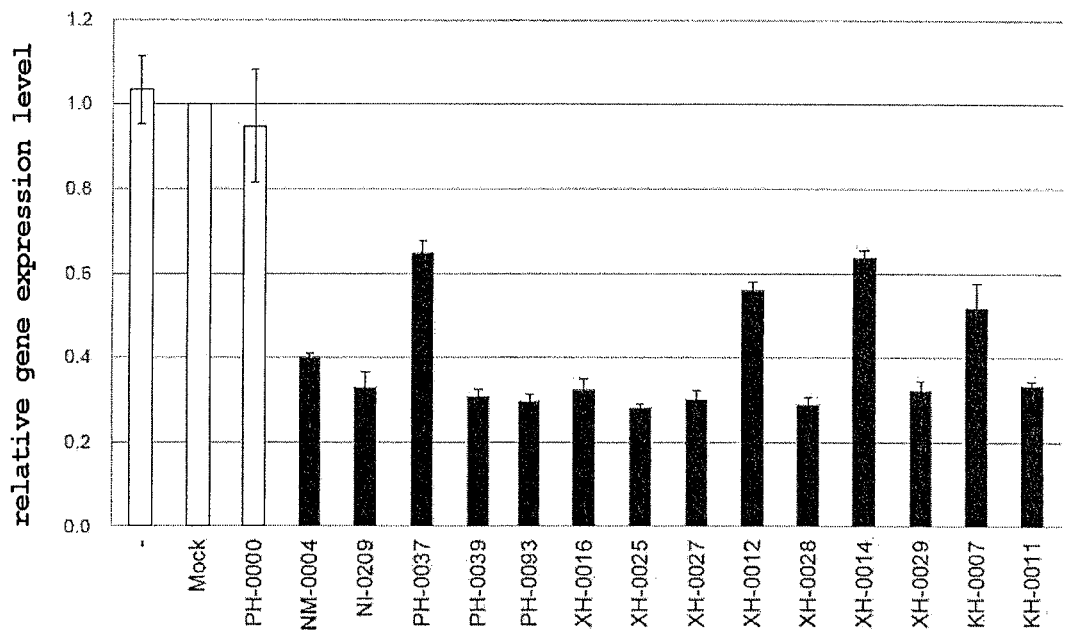
FIG. 9 is a graph showing the relative values of MET mRNA amount in Example 3 of the present invention.

As shown in FIGS. 8 and 9, the expression suppressive effect of AXL mRNA and MET RNA was maintained even when the non-nucleotide structure of the linker region was altered or the additional sequence of X region was deleted or extended.

Example 4

Various artificial match-type miRNAs of the present invention were synthesized based on the guide strand of mature let-7a, and a suppressive effect on the expression of the target gene HMGA2 mRNA was examined.

(1) Synthesis of miRNA

As a positive control, a molecule wherein the guide strand (SEQ ID NO: 2) of mature let-7a and a passenger strand (SEQ ID NO: 34) are linked via a loop region of natural type pre-let-7a (NM-0003) and a double stranded match-type RNA wherein the guide strand of mature let-7a and a sequence completely complementary thereto are annealed (NI-0207) were synthesized.

```
NM-0003 (72 mer)
     U   GU                       UUAGGGUCACAC          (SEQ ID
      GAG  AGUAGGUUGUAUAGUU                   C         NO: 35)
     CU-UUC  UCAUCUAACAUAUCAA               A
        *  UG    *           UAGAGGGUCACC
          **

NI-0207 (22/22 mer)
     UGAGGUAGUAGGUUGUAUAGUU                 (SEQ ID
     CUACUCCAUCAUCCAACAUAUC                 NO: 2)
     = ==    =                              (SEQ ID
                                            NO: 34)
```

In the following sequences, the underlined part shows the aforementioned guide strand sequence.

```
NM-0003
                                          (SEQ ID NO: 35)
5'-UGAGGUAGUAGGUUGUAUAGUUUAGGGUCACACCCACCACUGGGAG

AUAACUAUACAAUCUACUGUCUUUC-3'

NI-0207
      guide strand (SEQ ID NO: 2)/passenger strand
                                          (SEQ ID NO: 34)
5'-UGAGGUAGUAGGUUGUAUAGUU-3'/5'-CUAUACAACCUACUACCU

CAUC-3'
```

As shown below, various artificial match-type let-7a wherein linkers of proline derivative ([P]), terephthalic acid derivative ([TP]), glycine derivative ([Gly]), glycylglycine derivative ([GlyGly]) and lysine derivative ([K]) are introduced between X region comprising the guide strand sequence of mature let-7a and an additional sequence (0, 3 or 5 base length) on the 3'-side thereof, and Y region which is completely complementary to the X region and having a 2 base-length overhang on the 5'-side, as in Example 3, were synthesized.

```
            (SEQ ID NO: 36)              (SEQ ID NO: 36)
PH-0013                         X-0010
UGAGGUAGUAGGUUGUAUAGUU          UGAGGUAGUAGGUUGUAUAGUU
                        P                                TP
CUACUCCAUCAUCCAACAUAUCAA        CUACUCCAUCAUCCAACAUAUCAA
```

```
                    (SEQ ID NO: 37)
PH-0015
UGAGGUAGUAGGUUGUAUAGUUUCC
                         P
CUACUCCAUCAUCCAACAUAUCAAAGG (SEQ ID NO: 38)
PH-0094
UGAGGUAGUAGGUUGUAUAGUUUCCGG
                           P
CUACUCCAUCAUCCAACAUAUCAAAGGCC (SEQ ID NO: 36)
XH-0008
UGAGGUAGUAGGUUGUAUAGUU
                     Gly
CUACUCCAUCAUCCAACAUAUCAA (SEQ ID NO: 36)
XH-0009
UGAGGUAGUAGGUUGUAUAGUU
                   GlyGly
CUACUCCAUCAUCCAACAUAUCAA (SEQ ID NO: 36)
KH-0005
UGAGGUAGUAGGUUGUAUAGUU
                      K
CUACUCCAUCAUCCAACAUAUCAA (SEQ ID NO: 37)
XH-0030
UGAGGUAGUAGGUUGUAUAGUUUCC
                         TP
CUACUCCAUCAUCCAACAUAUCAAAGG (SEQ ID NO: 38)
XH-0031
UGAGGUAGUAGGUUGUAUAGUUUCCGG
                           TP
CUACUCCAUCAUCCAACAUAUCAAAGGCC (SEQ ID NO: 37)
XH-0032
UGAGGUAGUAGGUUGUAUAGUUUCC
                         Gly
CUACUCCAUCAUCCAACAUAUCAAAGG (SEQ ID NO: 37)
XH-0033
UGAGGUAGUAGGUUGUAUAGUUUCC
                       GlyGly
CUACUCCAUCAUCCAACAUAUCAAAGG (SEQ ID NO: 37)
KH-0012
UGAGGUAGUAGGUUGUAUAGUUUCC
                          K
CUACUCCAUCAUCCAACAUAUCAAAGG
```

In the following sequences, the 5'-side region of each linker is X region; in the aforementioned X region, the underlined part is the aforementioned guide strand sequence, the rest is the aforementioned additional sequence, and the 3'-side region of each linker is Y region.

PH-0013
(SEQ ID NO: 36)
5'-UGAGGUAGUAGGUUGUAUAGUU-[P]-AACUAUACAACCUACUACCUCAUC-3'

PH-0015
(SEQ ID NO: 37)
5'-UGAGGUAGUAGGUUGUAUAGUUUCC-[P]-GGAAACUAUACAACCUACUACCUCAUC-3'

PH-0094
(SEQ ID NO: 38)
5'-UGAGGUAGUAGGUUGUAUAGUUUCCGG-[P]-CCGGAAACUAUACAACCUACUACCUCAUC-3'

XH-0010
(SEQ ID NO: 36)
5'-UGAGGUAGUAGGUUGUAUAGUU-[TP]-AACUAUACAACCUACUACCUCAUC-3'

XH-0030
(SEQ ID NO: 37)
5'-UGAGGUAGUAGGUUGUAUAGUUUCC-[TP]-GGAAACUAUACAACCUACUACCUCAUC-3'

XH-0031
(SEQ ID NO: 38)
5'-UGAGGUAGUAGGUUGUAUAGUUUCCGG-[TP]-CCGGAAACUAUACAACCUACUACCUCAUC-3'

XH-0008
(SEQ ID NO: 36)
5'-UGAGGUAGUAGGUUGUAUAGUU-[Gly]-AACUAUACAACCUACUACCUCAUC-3'

XH-0032
(SEQ ID NO: 37)
5'-UGAGGUAGUAGGUUGUAUAGUUUCC-[Gly]-GGAAACUAUACAACCUACUACCUCAUC-3'

XH-0009
(SEQ ID NO: 36)
5'-UGAGGUAGUAGGUUGUAUAGUU-[GlyGly]-AACUAUACAACCUACUACCUCAUC-3'

XH-0033
(SEQ ID NO: 37)
5'-UGAGGUAGUAGGUUGUAUAGUUUCC-[GlyGly]-GGAAACUAUACAACCUACUACCUCAUC-3'

KH-0005
(SEQ ID NO: 36)
5'-UGAGGUAGUAGGUUGUAUAGUU-[K]-AACUAUACAACCUACUACCUCAUC-3'

KH-0012
(SEQ ID NO: 37)
5'-UGAGGUAGUAGGUUGUAUAGUUUCC-[K]-GGAAACUAUACAACCUACUACCUCAUC-3'

As a negative control, PH-0000 synthesized in Example 3 was used.

(2) Measurement of Expression Level of HMGA2 Gene

Each of the aforementioned RNAs was dissolved in distilled water for injection (Otsuka Pharmaceutical Co., Ltd.) at 0.4 μmol/L, whereby an RNA solution was prepared.

A549 cells (DS Pharma Biomedical Co., Ltd.) were used as the cells. A 10% FBS-containing DMEM (Life Technologies) was used as the medium. The culture conditions were set to 37° C. and 5% $CO_2$.

First, the cells were cultured in the aforementioned medium, and the cultured solution was dispensed to a 24-well plate so that each well contained 400 μL of the cultured solution to achieve a density of 4×104 cells/well. The cells were transfected with the aforementioned RNA using a transfection reagent Lipofectamine RNAiMAX (Life Technologies) according to the protocol attached to the aforementioned transfection reagent. Specifically, the transfection was carried out by setting the composition per well as follows. In the following composition, (B) is Opti-MEM (Life Technologies), and (C) is 0.4 μmol/L aforementioned RNA solution and 98.5 μL in total of them was added. The final concentration of the aforementioned RNA in the aforementioned well was set to 0.2 nmol/L.

TABLE 3

(composition per well: μL)

| | |
|---|---|
| cultured solution | 400 |
| transfection reagent | 1.5 |
| (B) + (C) | 98.5 |
| total | 500 |

After the transfection, the cells in the aforementioned wells were cultured for 24 hours, and then, the RNA was collected using an RNeasy Mini Kit (Qiagen, Netherlands) according to the protocol supplied therewith. Subsequently, cDNA was synthesized from the aforementioned RNA by using Transcriptor First Strand cDNA Synthesis Kit (Roche) according to the protocol supplied therewith. Then, as shown below, PCR was carried out using the aforementioned synthesized cDNA as a template, and the expression level of the HMGA2 gene and that of GAPDH gene as an internal standard were measured. The aforementioned expression level of the HMGA2 gene was normalized with reference to that of the GAPDH gene mentioned above.

The aforementioned PCR was carried out using LightCycler 480 SYBR Green I Master (trade name, Roche) as a reagent and LightCycler 480 Instrument II (trade name, Roche) as an instrument (hereinafter the same). The aforementioned HMGA2 and GAPDH genes were amplified using the following primer sets, respectively.

```
PCR primer set for HMGA2 gene
                              (SEQ ID NO: 39)
5'-GAAGCCACTGGAGAAAAACG-3'

(SEQ ID NO: 40)
5'-CTTCGGCAGACTCTTGTGAG-3' primer set for GAPDH gene
                              (SEQ ID NO: 15)
5'-ATGGGGAAGGTGAAGGTCG-3'

(SEQ ID NO: 16)
5'-GGGTCATTGATGGCAACAATATC-3'
```

As control 1, regarding the cells to which 100 μL of the aforementioned solution (B) alone had been added to the aforementioned cultured solution, the expression levels of the genes also were measured (−). Furthermore, as control 2, regarding the cells subjected to the same transfection procedures as in the above except that the aforementioned RNA solution was not added and that the aforementioned (B) and 1.5 μL of the aforementioned (A) were added so that the total amount of (A) and (B) would be 100 μL, the expression level of the gene also was measured (mock).

As for the expression level of normalized HMGA2 gene, the relative value of the expression level in the cell introduced with each RNA was determined based on the expression level in the cells of the control (mock) as 1.

(3) Results

Figure 10:
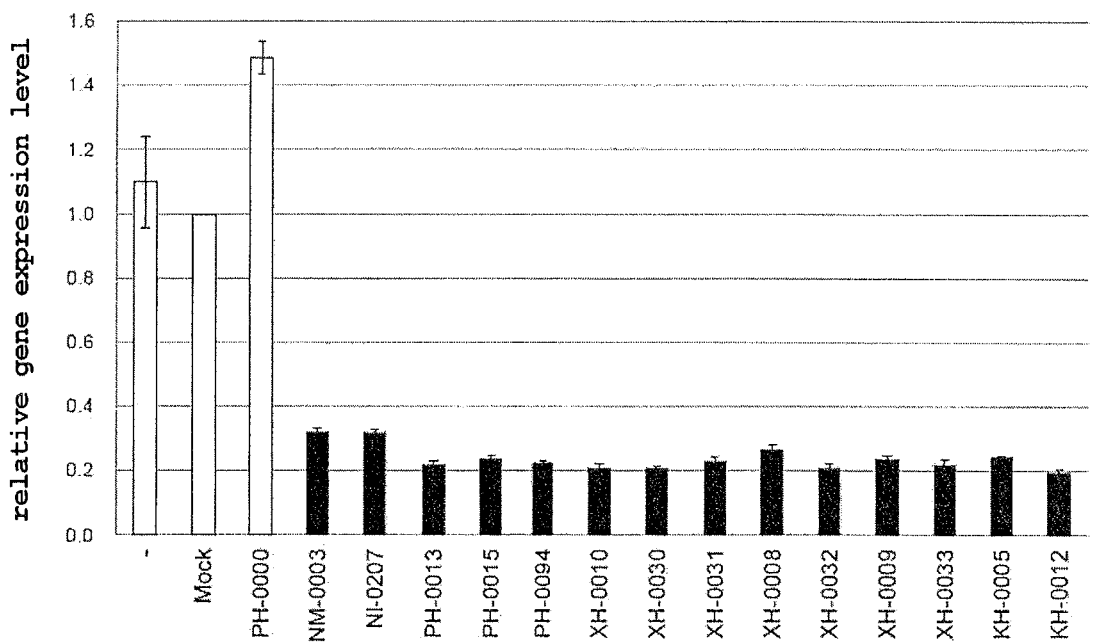
FIG. 10 is a graph showing the relative values of HMGA2 mRNA amount in Example 4 of the present invention.

As shown in FIG. 10, match-type let-7a of the Example suppressed expression of HMGA2 mRNA at the same level as or not less than that by the positive control mature let-7a and double stranded match-type let-7a. In addition, the expression suppressive effect of HMGA2 mRNA was maintained even when the non-nucleotide structure of the linker region or the base length of the additional sequence of X region was altered.

Example 5

Various artificial match-type miRNAs of the present invention were synthesized based on the guide strand of a mature miR-29b, and suppression effect on the expression of the target gene COLA1 mRNA was examined.

(1) Synthesis of miRNA

As a positive control, a molecule wherein the guide strand (SEQ ID NO: 5) of a mature miR-29b and a passenger strand (SEQ ID NO: 41) are linked via a loop region of natural type pre-miR-29b (NM-0005) and a double stranded match-type RNA wherein the guide strand of a mature miR-29b and a sequence completely complementary thereto are annealed (NI-0211) were synthesized.

```
NM-0005 (64 mer)
                                          (SEQ ID NO: 42)
   *   *   *        *    *UUAAA
  -GCUGGUUUCA AUGGUG UUAGAU      U
                                   A
 UU UGACUAAAGU UACCAC--GAUCUG   G
   G          U            UUAGU NI-0211 (23/23 mer)
 CACUGAUUUCAAAUGGUGCUAGA                  (SEQ ID NO: 41)
 UUGUGACUAAAGUUUACCACGAU                  (SEQ ID NO: 5)
```

In the following sequences, the underlined parts show the aforementioned guide strand sequences.

```
NM-0005
                                          (SEQ ID NO: 42)
5'-GCUGGUUUCAUAUGGUGGUUUAGAUUUAAAUAGUGAUUGUCUAGCAC

CAUUUGAAAUCAGUGUU-3'

NI-0211
  passenger strand (SEQ ID NO: 41)/guide strand (SEQ
                                              ID NO: 5)
5'-CACUGAUUUCAAAUGGUGCUAGA-3'/5'-UAGCACCAUUUGAAAUC

AGUGUU-3'
```

As shown below, various artificial match-type miR-29bs wherein linkers of proline derivative ([P]), terephthalic acid derivative ([TP]), glycine derivative ([Gly]), glycylglycine derivative ([GlyGly]) and lysine derivative ([K]) are introduced between X region comprising the guide strand sequence of a mature miR-29b and an additional sequence (0, 3 or 5 base length) on the 3'-side thereof, and Y region which is completely complementary to the X region and having a 2 base-length overhang on the 5'-side, as in Example 3, were synthesized.

| (SEQ ID NO: 43) | (SEQ ID NO: 43) |
|---|---|
| PH-0071 | XH-0034 |
| AACACUGAUUUCAAAUGGUGCUAGA | AACACUGAUUUCAAAUGGUGCUAGA |
| P | TP |
| UUGUGACUAAAGUUUACCACGAU | UUGUGACUAAAGUUUACCACGAU |

```
                                            (SEQ ID NO: 44)                                    (SEQ ID NO: 44)
PH-0073                                                      XH-0035
GGAAACACUGAUUUCAAAUGGUGCUAGA                                 GGAAACACUGAUUUCAAAUGGUGCUAGA
                                 P                                                        TP
CCUUUGUGACUAAAGUUUACCACGAU                                   CCUUUGUGACUAAAGUUUACCACGAU (SEQ ID NO: 45)                                    (SEQ ID NO: 45)
PH-0095                                                      XH-0036
CCGGAAACACUGAUUUCAAAUGGUGCUAGA                               CCGGAAACACUGAUUUCAAAUGGUGCUAGA
                                 P                                                        TP
GGCCUUUGUGACUAAAGUUUACCACGAU                                 GGCCUUUGUGACUAAAGUUUACCACGAU (SEQ ID NO: 43)                                    (SEQ ID NO: 44)
XH-0037                                                      XH-0038
AACACUGAUUUCAAAUGGUGCUAGA                                    GGAAACACUGAUUUCAAAUGGUGCUAGA
                                Gly                                                       Gly
UUGUGACUAAAGUUUACCACGAU                                      CCUUUGUGACUAAAGUUUACCACGAU (SEQ ID NO: 43)                                    (SEQ ID NO: 44)
XH-0039                                                      XH-0040
AACACUGAUUUCAAAUGGUGCUAGA                                    GGAAACACUGAUUUCAAAUGGUGCUAGA
                              GlyGly                                                     GlyGly
UUGUGACUAAAGUUUACCACGAU                                      CCUUUGUGACUAAAGUUUACCACGAU (SEQ ID NO: 43)                                    (SEQ ID NO: 44)
KH-0013                                                      KH-0014
AACACUGAUUUCAAAUGGUGCUAGA                                    GGAAACACUGAUUUCAAAUGGUGCUAGA
                                 K                                                         K
UUGUGACUAAAGUUUACCACGAU                                      CCUUUGUGACUAAAGUUUACCACGAU
```

In the following sequences, the 5′-side region of each linker is X region; in the aforementioned X region, the underlined part is the aforementioned guide strand sequence, the rest is the aforementioned additional sequence, and the 3′-side region of each linker is Y region.

PH-0071
(SEQ ID NO: 43)
5′-<u>UAGCACCAUUUGAAAUCAGUGUU</u>-[P]-AACACUGAUUUCAAAUGGUGCUAGA-3′

PH-0073
(SEQ ID NO: 44)
5′-<u>UAGCACCAUUUGAAAUCAGUGUUUCC</u>-[P]-GGAAACACUGAUUUCAAAUGGUGCUAGA-3′

PH-0095
(SEQ ID NO: 45)
5′-<u>UAGCACCAUUUGAAAUCAGUGUUUCCGG</u>-[P]-CCGGAAACACUGAUUUCAAAUGGUGCUAGA-3′

XH-0034
(SEQ ID NO: 43)
5′-<u>UAGCACCAUUUGAAAUCAGUGUU</u>-[TP]-AACACUGAUUUCAAAUGGUGCUAGA-3′

XH-0035
(SEQ ID NO: 44)
5′-<u>UAGCACCAUUUGAAAUCAGUGUUUCC</u>-[TP]-GGAAACACUGAUUUCAAAUGGUGCUAGA-3′

XH-0036
(SEQ ID NO: 45)
5′-<u>UAGCACCAUUUGAAAUCAGUGUUUCCGG</u>-[TP]-CCGGAAACACUGAUUUCAAAUGGUGCUAGA-3′

XH-0037
(SEQ ID NO: 43)
5′-<u>UAGCACCAUUUGAAAUCAGUGUU</u>-[Gly]-AACACUGAUUUCAAAUGGUGCUAGA-3′

XH-0038
(SEQ ID NO: 44)
5′-<u>UAGCACCAUUUGAAAUCAGUGUUUCC</u>-[Gly]-GGAAACACUGAUUUCAAAUGGUGCUAGA-3′

XH-0039
(SEQ ID NO: 43)
5′-<u>UAGCACCAUUUGAAAUCAGUGUU</u>-[GlyGly]-AACACUGAUUUCAAAUGGUGCUAGA-3′

XH-0040
(SEQ ID NO: 44)
5′-<u>UAGCACCAUUUGAAAUCAGUGUUUCC</u>-[GlyGly]-GGAAACACUGAUUUCAAAUGGUGCUAGA-3′

KH-0013
(SEQ ID NO: 43)
5′-<u>UAGCACCAUUUGAAAUCAGUGUU</u>-[K]-AACACUGAUUUCAAAUGGUGCUAGA-3′

KH-0014
(SEQ ID NO: 44)
5′-<u>UAGCACCAUUUGAAAUCAGUGUUUCC</u>-[K]-GGAAACACUGAUUUCAAAUGGUGCUAGA-3′

As a negative control, PH-0000 synthesized in Example 3 was used.

(2) Measurement of Expression Level of COL1A1 Gene

Each of the aforementioned RNAs was dissolved in distilled water for injection (Otsuka Pharmaceutical Co., Ltd.) at 1 µmol/L, whereby an RNA solution was prepared.

A549 cells (DS PHARMA BIOMEDICAL) were used as the cell. As the medium, DMEM (Life Technologies) containing 10% FBS was used. The culture conditions were set to 37° C., 5% $CO_2$.

First, the cells were cultured in the aforementioned medium, and the cultured solution was dispensed to a 24-well plate so that each well contained 400 µL of the cultured solution to achieve a density of 4×10⁴ cells/well. The cells were transfected with the aforementioned RNA using a transfection reagent Lipofectamine RNAiMAX (Life Technologies) according to the protocol attached to the aforementioned transfection reagent. Specifically, the transfection was carried out by setting the composition per well as follows. In the following composition, (B) is Opti-MEM (Life Technologies), (C) is the aforementioned 1 µmol/L RNA solution, 98.5 µL in total of them was added. The final concentration of the aforementioned RNA in the aforementioned well was set to 0.5 nmol/L.

TABLE 4

(composition per well: µL)

| | |
|---|---|
| cultured solution | 400 |
| transfection reagent | 1.5 |
| (B) + (C) | 98.5 |
| total | 500 |

After the transfection, the cells in the aforementioned wells were cultured for 24 hours, and then, the RNA was collected using an RNeasy Mini Kit (Qiagen, Netherlands) according to the protocol supplied therewith. Subsequently, cDNA was synthesized from the aforementioned RNA by using Transcriptor First Strand cDNA Synthesis Kit (Roche) according to the protocol supplied therewith. Then, as shown below, PCR was carried out using the aforementioned synthesized cDNA as a template, and the expression level of the COL1A1 gene and that of GAPDH gene as an internal standard were measured. The aforementioned expression level of the COL1A1 gene was normalized with reference to that of the GAPDH gene mentioned above.

The aforementioned PCR was carried out using LightCycler 480 SYBR Green I Master (trade name, Roche) as a reagent and LightCycler 480 Instrument II (trade name, Roche) as an instrument (hereinafter the same). The aforementioned COL1A1 and GAPDH genes were amplified using the following primer sets, respectively.

```
PCR primer set for COL1A1 gene
                                         (SEQ ID NO: 46)
5'-CCCAAGGACAAGAGGCATGT-3'

(SEQ ID NO: 47)
5'-CCGCCATACTCGAACTGGAA-3'
```

```
-continued
primer set for GAPDH gene
                                         (SEQ ID NO: 15)
5'-ATGGGGAAGGTGAAGGTCG-3'

(SEQ ID NO: 16)
5'-GGGTCATTGATGGCAACAATATC-3'
```

As control 1, regarding the cells to which 100 µL of the aforementioned solution (B) alone had been added to the aforementioned cultured solution, the expression levels of the genes also were measured (−). Furthermore, as control 2, regarding the cells subjected to the same transfection procedures as in the above except that the aforementioned RNA solution was not added and that the aforementioned (B) and 1.5 µL of the aforementioned (A) were added so that the total amount of (A) and (B) would be 100 µL, the expression level of the gene also was measured (mock).

As for the expression level of normalized COL1A1 gene, the relative value in the cell introduced with each RNA was determined based on the expression level in the cells of the control (mock) as 1.

(3) Results

Figure 11:
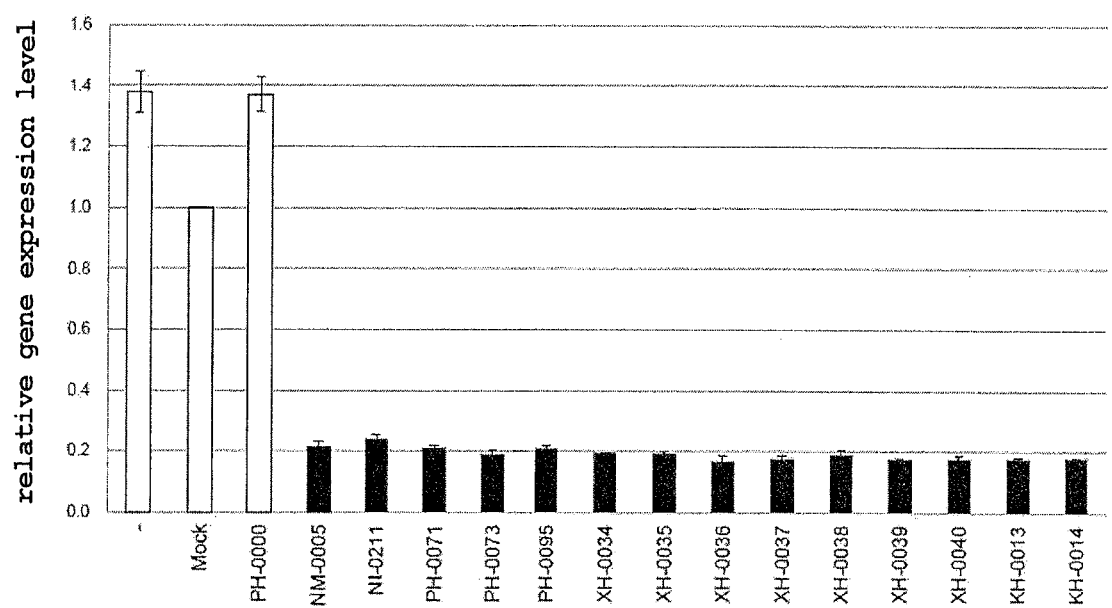
FIG. 11 is a graph showing the relative values of COLA1 mRNA amount in Example 5 of the present invention.

As shown in FIG. 11, match-type miR-29b of the Example suppressed expression of COLA1 mRNA at the same level as or not less than that by the positive control mature miR-29b and double stranded match-type miR-29b. In addition, the expression suppressive effect of COLA1 mRNA was maintained even when the non-nucleotide structure of the linker region or the base length of the additional sequence of X region was altered.

While the present invention has been described above with reference to illustrative embodiments, the present invention is by no means limited thereto. Various changes that may become apparent to those skilled in the art may be made in the configuration and specifics of the present invention without departing from the scope of the present invention. In addition, the contents disclosed in any publication cited herein, including patents and patent applications, are hereby incorporated in their entireties by reference, to the extent that they have been disclosed herein.

This application is based on a patent application No. 2013-273033 filed in Japan (filing date: Dec. 27, 2013), the contents of which are incorporated in full herein.

INDUSTRIAL APPLICABILITY

Since the artificial match-type miRNA of the present invention can be easily synthesized at a low cost, and can suppress the translation of a protein encoded by the aforementioned gene. Therefore, an artificial match-type miRNA of the present invention is useful as, for example, a pharmaceutical product, a diagnostic agent, an agricultural chemical, and a tool for conducting research on agriculture, medical science, life science, and the like.

The invention claimed is:

1. A single-stranded nucleic acid comprising an X region and a Y region,
wherein
the 3'-terminal of said X region and the 5'-terminal of said Y region are linked via a linker region of a non-nucleotide structure,
said X region comprises (i) a guide strand sequence of a mature miRNA and (ii) an additional sequence linked to the 3'-terminal of said guide strand sequence, wherein the additional sequence is UCCGG,
said Y region comprises a sequence completely complementary to said X region, and
said linker region comprises an amino acid residue, wherein the amino acid residue is represented by chemical formula

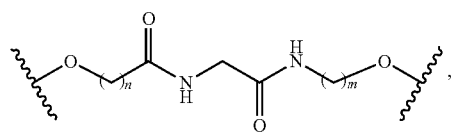
(I-1)

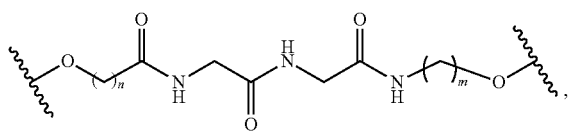
(I-4)

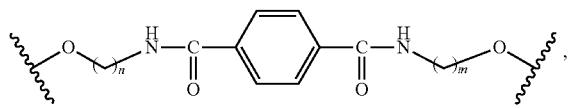
(I-6)

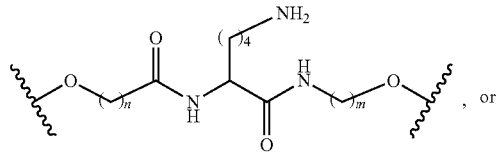
(I-7)
, or

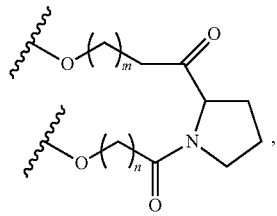
(II-8)

wherein n is an integer of 0-30, and m is an integer of 0-30.

2. The single-stranded nucleic acid according to claim 1, wherein when said Y region and said X region are aligned, said Y region has an overhang on the 3'-terminal.

3. The single-stranded nucleic acid according to claim 2, wherein said overhang has a 1-4 base length.

4. The single-stranded nucleic acid according to claim 1, wherein said X region has a length of 19-33 bases, and/or said Y region has a length of 21-35 bases, and/or the full length miRNA has a 40-68 base length.

5. The single-stranded nucleic acid according to claim 1, wherein,
(i) in said chemical formula (I-1), n=11 and m=12, or n=5 and m=4;
(ii) in said chemical formula (I-4), n=5 and m=4;
(iii) in said chemical formula (I-6), n=4 and m=4; or
(iv) in said chemical formula (I-7), n=5 and m=4.
(v) in said chemical formula (II-8), n=5 and m=4.

6. The single-stranded nucleic acid according to claim 1, wherein said X region comprises a guide strand sequence of a mature miRNA selected from the group consisting of hsa-miR-34, hsa-miR-29 and hsa-let-7.

7. A pharmaceutical composition comprising the single-stranded nucleic acid according to claim 1.

8. A method of suppressing expression of a target gene in a cell, a tissue, or an organ that expresses said gene, comprising administering single-stranded nucleic acid according to claim 1 to said cell, tissue, or organ.

9. A method of treating a disease, comprising a step of administering the single-stranded nucleic acid according to claim 6 to a subject, wherein a target gene for said single-stranded nucleic acid is involved in said disease.

* * * * *